(12) United States Patent
Labarbe et al.

(10) Patent No.: US 12,138,472 B2
(45) Date of Patent: Nov. 12, 2024

(54) TREATMENT DEVICE FOR DELIVERING A TREATMENT PLAN FOR FLASH DEPOSITION WITH AN ACCELERATOR OF CHARGED PARTICLES BY PENCIL BEAM SCANNING

(71) Applicant: Ion Beam Applications, Louvain-la-neuve (BE)

(72) Inventors: Rudi Labarbe, Louvain-la-neuve (BE); Lucian Hotoiu, Louvain-la-neuve (BE); Arnaud Pin, Louvain-la-neuve (BE); Yves Claereboudt, Louvain-la-neuve (BE); Gabriel Krier, Louvain-la-neuve (BE)

(73) Assignee: Ion Beam Applications, Louvain-la-neuve (BE)

( * ) Notice: Subject to any disclaimer, the term of this patent is extended or adjusted under 35 U.S.C. 154(b) by 386 days.

(21) Appl. No.: 17/811,172

(22) Filed: Jul. 7, 2022

(65) Prior Publication Data

US 2023/0023312 A1    Jan. 26, 2023

(30) Foreign Application Priority Data

Jul. 9, 2021 (EP) .................................. 21184673

(51) Int. Cl.
*A61N 5/10*        (2006.01)
(52) U.S. Cl.
CPC ............. *A61N 5/10* (2013.01); *A61N 5/1031* (2013.01); *A61N 2005/1088* (2013.01)
(58) Field of Classification Search
CPC ...... A61N 5/10; A61N 5/1031; A61N 5/1043; A61N 2005/1088; A61N 2005/1087

(Continued)

(56) References Cited

U.S. PATENT DOCUMENTS

2022/0126117 A1*  4/2022  Voronenko ........... A61N 5/1043
2024/0131361 A1*  4/2024  Labarbe ............... A61N 5/1043

FOREIGN PATENT DOCUMENTS

| EP | 3421085 | 1/2019 |
|----|---------|--------|
| WO | WO2018132847 | 7/2018 |
| WO | WO2020185544 | 9/2020 |

OTHER PUBLICATIONS

Jolly Simon et al., "Technical Challenges For FLASH Proton Therapy," Physica Medica, Acta Medica Edizioni E Congressi, Rome, IT, vol. 78 (Sep. 15, 2020) pp. 71-82.

* cited by examiner

*Primary Examiner* — Kiet T Nguyen
(74) *Attorney, Agent, or Firm* — FINNEGAN, HENDERSON, FARABOW, GARRETT & DUNNER, LLP

(57) ABSTRACT

A treatment device includes a pulsed particles accelerator and a processor for controlling the latter to deliver a treatment plan by deposition at HDR of charged particles into a flash volume (Vht) by PBS. To shorten the time for depositing a target dose (Dti) into the cells spanned by the flash spots (Si) of the flash volume (Vht), the flash spots are combined into k sets of n flash spots (Si). After depositing a $j^{th}$ pulse dose (Dij) into the cells spanned by a $i^{th}$ flash spot (Si) the beam commutes from the ith flash spot (Si) to a next (i+1)th flash spot according to a flash scanning subsequence to deposit a jth dose into the cells spanned by each of the subsequent flash spots of the flash scanning subsequence, until returning to the ith flash spot to deposit a (j+1)th dose (Di(j+1)), and so on When all the cells spanned by all the flash spots of a set have received their corresponding target dose, the beam moves to a next set of combined flash spots and repeats the foregoing pulse deposition steps.

7 Claims, 12 Drawing Sheets

(58) Field of Classification Search
USPC .................................................. 250/492.3
See application file for complete search history.

TREATMENT DEVICE FOR DELIVERING A TREATMENT PLAN FOR FLASH DEPOSITION WITH AN ACCELERATOR OF CHARGED PARTICLES BY PENCIL BEAM SCANNING

CROSS REFERENCE TO RELATED APPLICATIONS

This application claims priority of European patent application no. 21184673.8 filed on Jul. 9, 2021, which is incorporated herein by reference in its entirety.

TECHNICAL FIELD

The present disclosure relates to a treatment device for delivering a plan for treatment with a beam of charged particles, e.g., protons, of a treatment volume (V) including a flash volume (Vht) including healthy cells and tumoral cells.

BACKGROUND

Radiation therapy with particles or waves, such as electron beams, protons beams, heavy ions beams, x-rays, γ rays and the like, has become a tool for treating patients with tumors.

Since both tumoral cells and healthy cells comprised in a volume are damaged by such radiations, a challenge in cancer treatment is to define a treatment plan ensuring that the tumoral cells are effectively destroyed or killed, while sparing as much as possible the healthy cells, in particular those adjacent to the tumoral cells. A typical step of a treatment plan is the capture of images of the tumoral region by CT scan. Based on these images, an oncologist identifies the right targets and determines the locations and doses to be deposited to kill the tumoral cells. Such plan must satisfy multiple, often competing, parameters, and is therefore quite complex. For this reason, treatment planning systems are generally computer generated.

A first criterion a treatment plan must fulfil is to ensure that, at the end of the treatment, a total target dose sufficient to kill the tumoral cells is delivered into the volume. At the same time, a second criterion to be fulfilled by the treatment plan is to minimize the degradation of the healthy cells adjacent to the tumoral cells. No matter how accurate the dose deposition is in a volume comprising tumoral cells, a radiation beam reaching the volume comprising the tumoral cells almost necessarily crosses healthy cells and delivers thereto a dose also to healthy cells surrounding or included in that volume. Different radiations deposit their energies in different patterns. For example, X rays deposit most of their energy near the level of the skin, and the deposited energy decreases with depth. Healthy tissues located upstream of a target volume of tumoral cells therefore receive a higher dose than the tumoral cells of target volume. By contrast, as shown in FIGS. 1A & 1C, charged particle beams, in particular protons, deposit most of their energy close to the end of their beam path, forming a so called Bragg peak.

Pencil beam scanning (PBS) is a technique of steering a beam of charged particles towards individual spots of a mesh of spots defining a target volume comprising tumoral cells. Predefined target doses are thus deposited into the cells spanned by the individual spots. The beam steering and dose deposition proceed according to a treatment plan defining the charge to be deposited at each spot and the scanning sequence of spots. PBS reduces unnecessary radiation exposure to surrounding non-cancerous cells by shaping the area being treated to mirror the tumour geometry. Beside the geometry of the target, PBS allows local tuning of the intensity of a beam depending on the position of the spot within the target.

The mesh of spots generally comprises several painting layers, each painting layer consisting of a 2D array of spots arranged on a plane normal to the irradiation axis (X). The sequential arrangement of several painting layers defines a whole of the target volume by the thus obtained mesh of spots. With accelerated proton beams, one beam can successively deposit a predefined charge at a corresponding spot of each painting layer by superimposing a number of Bragg peaks staggered in depth at each painting layer along an irradiation axis (X). This results in Spread Out Bragg Peaks (SOBP) spanning a whole depth of the volume of tumoral cells or of a fraction of that volume. This technique allows delivering the target doses into the target volume by PBS in several painting layers of different beam energies. The painting layer (or depth) into which a dose is deposited can be controlled, i.e., by an energy of the accelerated particles. The dose deposited into the cells spanned by a spot in the painting layer is controlled, i.e., by a fluence (=number of charges per unit area) of the beam. With a deposition pattern linked to the shape of the Bragg Peak, the healthy cells located upstream of the target volume crossed by a proton beam receive a lower dose than the cells in the volume. Care must be taken, however, when designing the treatment plan, that the cells spanned by spots of a given painting layer receive doses which sum up with previously deposited doses each time a dose is deposited into cells spanned by corresponding spots located in a painting layer downstream of the given painting layer. The terms "downstream" and "upstream" are used herein relative to the direction of propagation of the beam.

With SOBP as described above for proton beams, the healthy cells located upstream of the target volume receive a substantially lower dose than the cells comprised within the target volume. On the other hand, the healthy cells in or adjacent to the target volume receive similar doses as the adjacent tumoral cells in the same target volume. One principle of radiotherapy is that the healthy cells are generally (slightly) more resistant to radiation than tumoral cells. A key of radiotherapy is to "open the therapeutic window", i.e., find a dose such that the tumour is damaged and the healthy tissue is preserved. This window is, however, quite narrow. To minimize the degradation of the healthy cells adjacent to the tumoral cells, the total dose received by a healthy cell must not exceed a maximum allowable dose. As the maximum allowable dose a healthy cell can (relatively) safely receive in one session may be substantially similar to the minimum target dose required to destroy the tumoral cells, there is a tradeoff to be found between two incompatible requirements: on the one hand depositing a dose sufficient to kill tumoral cells and, on the other hand, depositing a dose sparing healthy cells. This problem is reduced, albeit not solved, by spreading the treatment over several sessions.

The total target dose is often delivered to the tumoral cells in one or more fractions (or sessions) separated in time. Fractionating the doses deliveries is a way of opening further the therapeutic window. The sum of the dose delivered at each session should reach the total target dose required to kill the tumoral cells taking account of the healing of the cells during the time between two sessions. It has been observed that, compared with healthy cells, the tumoral cells have a longer recovery time to recover from the damages suffered after an irradiation fraction. This suggests increasing the number of sessions to allow healthy cells to heal better than tumoral cells. A session is, however, quite uncomfortable for the patient, so that reducing the number of sessions is advantageous for the patient's comfort and is more cost effective.

Historically, treatment plans by radiation therapy included the delivery of radiation doses to the treated cells at a conventional dose deposition rate (CDR) lower than 1 Gy/s, generally of the order of 0.03 Gy/s. The dose deposition rate at one cell by all the spots overlapping this cell during one session is defined as a ratio $\Sigma_j D_{ij}/\Sigma_j t_j$ of the sum of doses $(D_{ij})$ deposited in the cell (i) by the spots during the session to the sum of the times $(t_j)$ required for depositing a corresponding dose $(D_{ij})$. With rare exceptions, current radiation therapy facilities deliver dose-rates <0.1 Gy/s, preferably of the order of 0.03 Gy/s and most clinical protocols involve delivery at regular intervals of a plurality of target doses $(D_{ti})$ of 2 to 3 Gy at every session, cumulated to reach the total target dose which is often close to the tolerance limit of normal tissues located in the radiation field, thus potentially damaging them together with the tumoral cells. Recently, it has been observed that a same dose deposited at ultra-high dose deposition rate (HDR) had a significantly lower effect on healthy cells compared with the same total dose deposited at conventional dose deposition rates (CDR). This difference of behaviour between CDR and HDR was, however, not observed with tumoral cells. HDR can be one or more orders of magnitude larger than conventional dose deposition rates (CDR) usually applied. Deposition of a dose at ultra-high dose deposition rates (HDR) is also referred to as FLASH-radiotherapy (=FLASH RT). It has been observed experimentally on animals and on various organs, that dose deposition at HDR can significantly spare healthy tissues in comparison with conventional deposition of a same dose at CDR and, at the same time, tumoral cells respond the same or even better to HDR deposition than to CDR deposition. For example, FLASH-RT reportedly elicits in mice a dramatic decrease of the incidence of lung fibrosis, of memory loss subsequent to brain irradiation, and of necrosis of the small intestine while keeping the anti-tumor efficiency unchanged. Such specific normal tissue sparing has been confirmed in large animals and a patient with cutaneous lymphoma has already been treated with FLASH-RT. Target doses $(D_{tj})$ of the order of 10 to 15 Gy can thus be deposited at one FLASH-RT session. FLASH-RT offers the advantage of increasing the therapeutic window while requiring fewer sessions or fractions than with conventional dose deposition sessions.

Particles are accelerated up to a speed of ⅓ of the speed of light (c). As the speed of the charged particles approaches the speed of light, relativistic effects must be compensated and either the frequency of the electrical field or the magnetic field must be modified to compensate the increase of the mass of the charged particles as their velocity becomes high. Relativistic effects become significant at about $v \approx c/3$, with v=particles speed and c=light speed. For example, in synchrocyclotrons the frequency of the driving RF electric field is varied during the acceleration path followed by the charged particles, while keeping the magnetic field constant. In synchrotons, on the other hand, the magnetic field is increased with time during the accelerating process, while the frequency of the driving RF electric field is maintained constant. Charged particles can also be accelerated to high speeds with a laser driven ion accelerator.

To allow the magnetic field or the RF frequency of the electric field to be varied during the acceleration process, the charged particles must be accelerated by successive batches, so that all charged particles are exposed to the magnetic field and RF frequency corresponding to their speed. Consequently, the charged particles are emitted by pulses (Pij), each pulse corresponding to a batch of charged particles having a pulse charge (Cij) which is limited to a maximum pulse charge (i.e., $C_{ij} \leq CM$). Each pulse has a duration of pulse time (tp), and the pulses are separated from one another by an interpulse interval ($\Delta tp$). The foregoing parameters are dependent on the particle accelerator used. It must be ensured that the maximum pulse charge (CM), the interpulse interval ($\Delta tp$), and the number (N) of pulses required to deposit the target dose in a given subvolume, are compatible with HDR (i.e., the beam current $N \times CM/[(N-1) \times \Delta tp]$ is sufficiently large so that the dose rate in the tissue $\geq 1$ Gy/s).

Because each spot (Si) of a given painting layer receives doses which sum up with previously deposited doses each time it is irradiated by a beam of charge (Cij) which deposits a dose (Dij) along the beam path at various spots located in painting layers downstream of the given painting layer, it is not possible to deposit doses at HDR with more than one painting layer. Indeed, the time denominator in the dose deposition rate ratio ($\Sigma_j D_{ij}/\Sigma_{ij} t_j$) becomes rapidly too high for the cells located most upstream in the target volume, which repeatedly receive small doses (Dj) during times (tj) each time a spot downstream is being targeted. PBS with a single painting layer can be achieved with proton beams by depositing with a single beam the doses according to a SOBP over a whole subvolume whose cross section is defined by a spot and spanning over a whole depth of the volume extending along the irradiation axis (X). The subvolume can be a cylinder whose base is a spot and extending along the irradiation axis (X).

Depending on the spacing between neighbouring spots in the 2D array, it is likely that a beam aimed at a given spot delivers some dose to the cells spanned by neighbouring spots too. This is because the charge fluence (=number of charges per unit area) in a beam can be defined by a Gaussian curve. It is generally considered that the overlapping between Gaussian curves over neighbouring spots leads to a substantially uniform fluence when the spots are separated by a distance of ca. 1.5σ of the Gaussian distribution of charges across the beam cross-section. Overlapping of the Gaussian spot profile is desired to ensure that no portion of the target volume has not received the predefined target dose and that the fluence is uniform between neighbouring spots. The overlap of charges and consecutive prolonged duration of dose deposition are, however, quite detrimental to FLASH RT, since each time a dose is deposited into cells spanned by a neighbouring spot by overlap, it decreases the dose deposition rate into the neighbouring spot by increasing the $\Sigma_j t_j$ denominator of the dose deposition rate ratio, which can become incompatible with HDR. This problem is further increased with PBS deposition, because the target doses to be deposited at HDR into each subvolume must generally be deposited with several pulses. Indeed, the target doses are generally higher than can be delivered by a single pulse of maximum pulse charge (CM). Depositing the target doses in several pulses prolongs the deposition time, $\Sigma_j t_j$, into a subvolume but also into neighbouring subvolumes by overlapping.

The foregoing constraints render dose deposition at HDR by PBS very complex. The present disclosure overcomes the aforementioned problems by ensuring that a target volume treated by PBS of charged particles is effectively irradiated at HDR where required taking account of any overlapping dose deposition distribution of all charges overlapping or leaking over a given spot to be treated. These and other advantages are described in more detail herein.

SUMMARY

In accordance with the present disclosure, there is provided a treatment device for treatment with a beam (100) of charged particles, of a treatment volume (V), the treatment volume (V) comprising a target volume (Vt) including substantially only tumoral cells (3t) and a flash volume (Vht) including healthy cells (3h) and tumoral cells (et), the treatment device comprising:

- a pulsed particles accelerator configured to deliver pulses of charged particles for depositing doses (Dij) into the treatment volume (V) by pencil beam scanning (PBS), spot by spot (Si, Ri) distributed over a single painting layer spanning the whole treatment volume (V), such that the doses are deposited into the spots (Si) enclosed within the flash volume (Vht) at a ultra high dose deposition rate (HDR), wherein HDR is defined as a dose rate, HDR≥1 Gy/s, wherein charged particles are emitted by pulses (Pij), each pulse having a pulse charge (Cij) smaller than or equal to a maximum pulse charge (CM) and a duration of pulse time (tp), and the pulses are separated from one another by an interpulse interval (Δtp), and the beam of charged particles can scan from a first flash spot to a second flash spot at a maximum scan speed (vs=ds/Δts), wherein ds is a distance between the first and second flash spots, and Δts is a scan time required for scanning from the first to the second flash spot; and
- a processor configured to control the pulsed particles accelerator to implement a treatment plan (TP), wherein the treatment plan comprises: a definition of a mesh of N flash spots (Si) covering an area of a projection parallel to an irradiation axis (X) substantially parallel to the beam (100) of the flash volume (Vht) onto a projection plane (π) normal to the irradiation axis (X); a definition for each flash spot (Si), of a target charge (Cti) required for depositing a target dose (Dti) into the cells spanned by each flash spot (Si); a definition of a theoretical flash charge planning for each flash spot (Si), including a theoretical pulse charge (Cij) of a number (mi) of pulses required for depositing the target dose (Dti) into the cells spanned by each flash spot (Si), wherein the target charge (Cti) is equal to a sum of the number (mi) of theoretical pulse charges (Cij) irradiating a flash spot (i.e., $Cti=\Sigma_{j=1}^{mi} Cij$), or wherein the target dose (Dti) is equal to a sum of the number (mi) of pulse doses (Dij) deposited into the cells spanned by the flash spot by each pulse charge (Cij) (i.e., $Di=\Sigma_{j=1}^{mi} Dij$); and a definition of a flash scanning sequence of the N flash spots, including a sequence of flash spots (Si) on which the corresponding number (mi) of pulse doses (Dij) are to be deposited into the cells spanned by each flash spot, wherein the flash scanning sequence comprises: a definition of a number (k) of sets, each set comprising a number n of flash spots (Si), wherein 1<n<N; and a definition for each set of n combined flash spots, of a flash scanning subsequence of the n combined flash spots, such that the distance (ds) between every first and second consecutive flash spots ((Si, S(i+1)) and (Sn, S1)) of the set is always lower than or equal to a maximum distance (dM) defined as a product of the scan speed (vs) and a dead time (td) (i.e., d≤dM=vs×td), wherein the dead time (td) is a time between the end of a pulse and a beginning of a next pulse (i.e., td=Δtp−tp), and wherein the processor is configured for controlling the pulsed particles accelerator to:

(a) point the beam at a first flash spot (S1), i.e., i=1, and deliver a first pulse charge (C11), i.e., with j=1, to deposit a corresponding first pulse dose (D11) into the cells spanned by a first flash spot (S1) of a first flash scanning subsequence of a first set of n combined flash spots;

(b) move the beam to a second flash spot (S2) of the flash scanning subsequence, i.e, i=2, and deliver a first pulse charge (C21) to deposit a first pulse dose (D21) into the cells spanned by the second flash spot (S2) during an estimated time required for measuring during a treatment session an actual first pulse charge (C11) actually delivered at the first flash spot (S1) and compute an adjusted theoretical second pulse charge (C12) to be next delivered at the first flash spot (S1) to align with the theoretical flash charge planning;

(c) if i<n, move the beam to an ith flash spot (Si) in the flash scanning subsequence, deliver a first pulse charge (Ci1) into the cells spanned by the ith flash spot (Si) during an estimated time required for measuring during a treatment session an actual previous pulse charge (C(i−1)1) actually delivered at a previous flash spot (S(i−1)) and compute an adjusted theoretical second pulse charge (C(i−1)2) to be next delivered at the previous flash spot (S(i−1)) to align with the theoretical flash charge planning;

(d) repeat the previous step (n−3) times until i=n;

(e) return the beam to the first flash spot (S1) of the flash scanning subsequence, and deposit the adjusted theoretical second pulse charge (C12) thus computed at the first flash spot (S1), during an estimated time required for measuring during a treatment session an actual first pulse charge (Cn1) delivered at the nth flash spot (Sn) and computing an adjusted theoretical second pulse charge (Cn2) to be next delivered at the nth flash spot (Sn) to align with the theoretical flash charge planning;

(f) repeat (b) to (e) until j=(mi−1) and repeat (b) to (d) for j=mi, at least until the target charge (Cti) has been delivered to each flash spot (S1, Sn) of the first set of n combined flash spots;

(g) move the beam to a first flash spot according to a second flash scanning subsequence of a second set of n combined flash spots and repeat (a) to (f) for the n combined flash spots of the second set of n combined flash spots; and (h) repeat a last step to the flash scanning subsequences of the remaining (k−2) sets of n combined flash spots until the corresponding target charges (Cti) is delivered at HDR to the n combined flash spots of all k sets of the mesh.

DETAILED DESCRIPTION

Figure 1A:
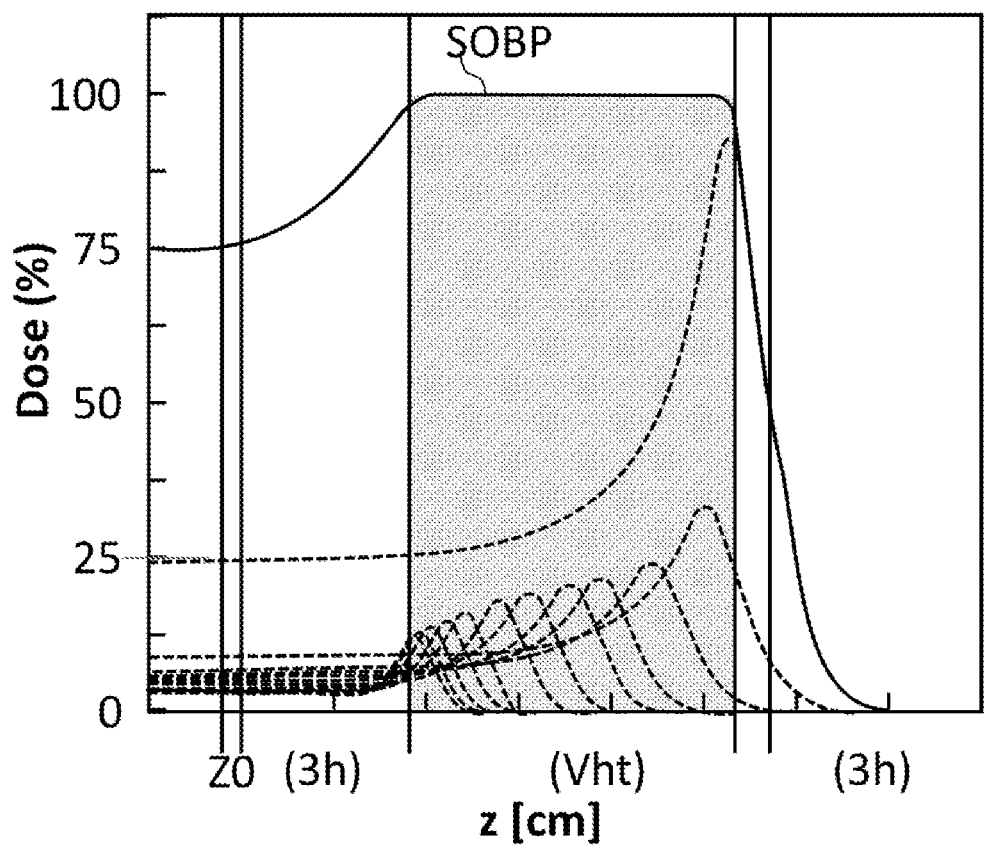
FIG. 1A shows an example of Spread Out Bragg peak (SOBP).
Figures 1B, 1C:
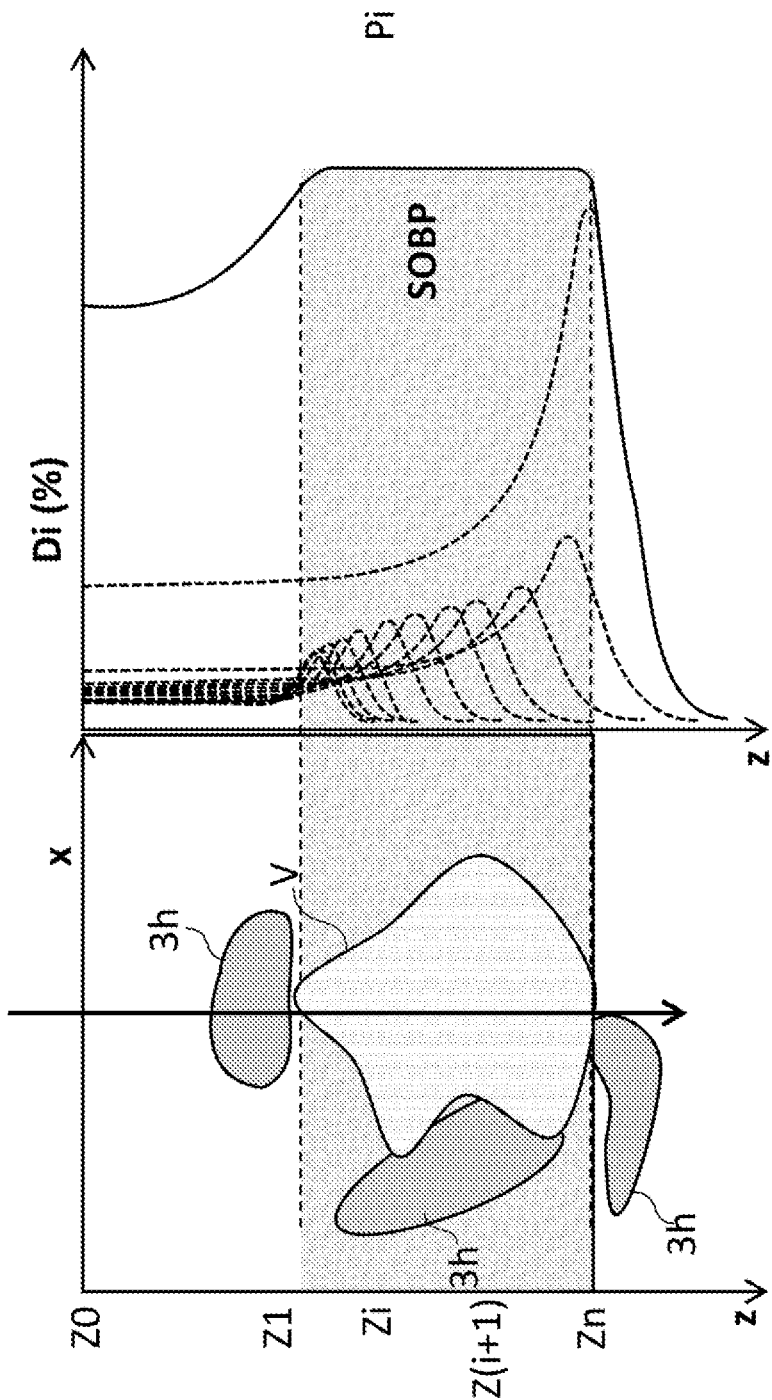
FIG. 1B shows an example of irradiation of a target volume comprising tumoral cells, surrounded by healthy tissues.
FIG. 1C shows the SOBP obtained with a proton beam along a given irradiation axis (X).

To spare healthy cells and kill tumoral cells, doses must be deposited into a flash volume (Vht) at ultra high deposition rates (HDR). The beam is emitted by a pulsed particles accelerator delivering pulses of charged particles. Several pulses of the pulsed beam are generally required to deposit the target doses into the flash volume (Vht), which may prolong the deposition time beyond the limits for yielding HDR. A treatment plan according to the present disclosure permits depositing at HDR target doses at predefined positions within the flash volume (Vht) by pencil beam scanning (PBS), spot by spot distributed over a single painting layer spanning the whole flash volume.

The present disclosure concerns a treatment device for delivering a plan for treatment with a beam of charged particles, preferably of protons, of a treatment volume (V) composed of, a target volume (Vt) including substantially only tumoral cells and of a flash volume (Vht) including healthy cells and preferably tumoral cells (3t).

For example, the target volume (Vt) can be defined as a gross tumor volume (GTV), which mainly contains tumoral cells. The treatment volume can include a clinical target volume (CTV) which is defined as the area in which the therapist wants to deliver the required dose. If, on the one hand, the treatment volume corresponds to the CTV (i.e., the flash volume (Vht) is enclosed in the CTV), the CTV would be the combination of the GTV (or target volume (Vt)) with the flash volume (Vht) and would therefore contain tumoral and healthy cells. If, on the other hand, the treatment volume (Vt) includes the CTV and any organ positioned upstream of the CTV on the beam path which must be preserved, then the flash volume (Vht) would intersect with and extend beyond the CTV, by including said organs. With the present disclosure, the desired dose required kill the tumoral cells in the whole CTV is delivered and the HDR is applied to spare the healthy tissues contained in the flash volume (Vht).

The treatment device comprises a pulsed particles accelerator configured for delivering pulses of charged particles which deposit doses (Dij) into the treatment volume (V) by pencil beam scanning (PBS), spot by spot (Si, Ri) distributed over a single painting layer spanning the whole treatment volume (V), such that the doses are deposited into the spots (Si) enclosed within the flash volume (Vht) at a ultra high dose deposition rate (HDR), wherein HDR is defined as a dose rate, HDR≥1 Gy/s, and wherein the pulsed particles accelerator is characterized by the following properties:

the charged particles are emitted by pulses (Pij), each pulse having a pulse charge (Cij) smaller than or equal to a maximum pulse charge (CM≥Cij) and a duration of pulse time (tp), and the pulses are separated from one another by an interpulse interval (Δtp); and the beam of charged particles can scan from a first flash spot to a second flash spot at a maximum scan speed (vs=ds/Δts), wherein ds is a distance between the first and second flash spots, and Δts is a scan time required for scanning from the first to the second flash spot.

The treatment device comprises a computer or a processor configured for controlling the pulsed particles accelerator to implement a treatment plan (TP), wherein the treatment plan comprises:

defining a mesh of N flash spots (Si) covering an area of a projection parallel to an irradiation axis (X) substantially parallel to the beam (100) of the flash volume (Vht) onto a projection plane (π) normal to the irradiation axis (X);

for each flash spot (Si), defining a target charge (Cti) required for depositing a target dose (Dti) onto the cells spanned by each flash spot (Si);

determining a theoretical flash charge planning for each flash spot (Si), defining a theoretical pulse charge (Cij) of a number (mi) of pulses required for depositing the target dose (Dti) at the cells spanned by each flash spot (Si), wherein the target charge (Cti) is equal to a sum of the number (mi) of theoretical pulse charges (Cij) irradiating a flash spot (i.e., Cti=$\Sigma_{j=1}^{mi}$ Cij), or wherein the target dose (Dti) is equal to a sum of the number (mi) of pulse doses (Dij) deposited into the cells spanned by the flash spot by each pulse charge (Cij) (i.e., Di=$\Sigma_{j=1}^{mi}$ Dij); and defining a flash scanning sequence of the N flash spots, defining a sequence of flash spots (Si) on which the corresponding number (mi) of pulse doses (Dij) are to be deposited into each flash spot.

In certain aspects, the present disclosure concerns the flash scanning sequence which comprises:

defining a number (k) of sets (5), each set (5) comprising a number n of flash spots (Si), wherein 1<n<N, for each set (5) of n combined flash spots, defining a flash scanning subsequence of the n combined flash spots, such that the distance (ds) between every first and second consecutive flash spots ((Si, S(i+1)) and (Sn, S1)) of the set is always lower than or equal to a maximum distance (dM) defined as a product of the scan speed (vs) and a dead time (td) (i.e., d≤dM=vs× td), wherein the dead time (td) is a time between the end of a pulse and a beginning of a next pulse (i.e., td=Δtp−tp).

The processor is configured for controlling the pulsed particles accelerator such as,
  (a) to point the beam at a first flash spot (S1), i.e, i=1, and to deliver a first pulse charge (C11), i.e., with j=1, to deposit a corresponding first pulse dose (D11) into the cells spanned by a first flash spot (S1) of a first flash scanning subsequence of a first set of n combined flash spots;
  (b) to move the beam to a second flash spot (S2) of the flash scanning subsequence, i.e, i=2, and to deliver a first pulse charge (C21) to deposit a first pulse dose (D21) into the cells spanned by the second flash spot (S2) during an estimated time required for measuring during a treatment session an actual first pulse charge (C11) actually delivered at the first flash spot (S1) and computing an adjusted theoretical second pulse charge (C12) to be next delivered at the first flash spot (S1) to align with the theoretical flash charge planning;
  (c) if i<n, to move the beam to an ith flash spot (Si) in the flash scanning subsequence, to deliver a first pulse charge (Ci1) into the cells spanned by the ith flash spot (Si) during an estimated time required for measuring during a treatment session an actual previous pulse charge (C(i−1)1) actually delivered at a previous flash spot (S(i−1)) and computing an adjusted theoretical second pulse charge (C(i−1)2) to be next delivered at the previous flash spot (S(i−1)) to align with the theoretical flash charge planning;
  (d) to repeat the previous step (n−3) times until i=n;
  (e) to return the beam to the first flash spot (S1) of the flash scanning subsequence, i.e., i=1, and to deposit the adjusted theoretical second pulse charge (C12) thus computed at the first flash spot (S1), i.e., j=2, during an estimated time required for measuring during a treatment session an actual first pulse charge (Cn1) delivered at the nth flash spot (Sn) and computing an adjusted theoretical second pulse charge (Cn2) to be next delivered at the nth flash spot (Sn) to align with the theoretical flash charge planning;
  (f) to repeat the steps (b) to (e) until j=(mi−1) and to repeat the steps (b) to (d) for j=mi, at least until the target charge (Cti) has been delivered to each flash spot (S1, Sn) of the first set of n combined flash spots;
  (g) to move the beam to a first flash spot according to a second flash scanning subsequence of a second set of n combined flash spots and to repeat the steps (a) to (f) for the n combined flash spots of the second set of n combined flash spots; and
  (h) repeating the last step to the flash scanning subsequences of the remaining (k−2) sets of n combined flash spots until the corresponding target charges (Cti) is delivered at HDR to the n combined flash spots of all k sets (5) of the mesh.

The number (n) of combined flash spots in a set (5) can be defined as,
  a ratio tc/td 22 1, if tc/td is an integer (i.e., n=tc/td, if tc/td ∈ N), and
  a sum of unity and of an integer portion of the ratio (tc/td), (i.e., n=INTEGER (tc/td)+1), in all other cases,
wherein td is the dead time and tc is a computing time greater than the dead time (tc>td), required by the pulsed particles accelerator for defining and preparing a next pulse (P(j+1)) according to the adjusted theoretical pulse charge (Ci(j+1)) calculated on the basis of an actual pulse charge (Cij) measured on a first pulse (Pij) preceding the second pulse (Pi(j+1)). The number (k) of sets (5) of n combined flash spots can be defined as an integer portion of a ratio (N/n) (i.e., n=INTEGER (N/n)), and an additional set of nR flash spots can be defined and treated as the sets of n combined flash spots as defined above, wherein nR<n is a remainder of the ratio N/n, until the target charges (Cti) has been delivered at HDR to all N flash spots of the mesh.

In an embodiment, the number (n) of combined flash spots is 2 (i.e., n=2) and
  a second flash spot (S2) in the flash scanning subsequence of a first set of n=2 flash spots (S1, S2) must receive a number (m2) of pulses (P1 to Pm2) to reach a second target charge (Ct2)), which is higher than the number (m1) of pulses (P1 to Pm1) required to deliver a first target charge (Ct1) to the first flash spot (S1) (i.e., m1<m2 and Ct1<Ct2), and
  when the first and second flash spots (Si, S2) of the first set (5) have each received m1 pulses and the target charge (Ct1) was delivered to the first flash spot (S1) the second flash spot (S2) is dissociated from the first flash spot (S1) and is combined with a third flash spot (S3) to form a second set of n=2 flash spots (S2, S3), wherein the third flash spot (S3) is located at a distance d<DM from the second flash spot (S2) and must receive a third target charge (Ct3) larger than a residual charge (Ct2−Ct1), until both second flash spot (S2) and third flash spot (S3) have each received (m2−m1) pulses and the second flash spot (S2) has received the target charge (Ct2), and
  the third flash spot (S3) is dissociated from the second flash spot (S2) and is combined with a fourth flash spot (S4) to form a third set of n=2 flash spots (S3, S4), and so on until all N flash spots of the mesh have received their target charges (Cti) at HDR.

Generally, the computing time (tc) can be required to complete at least the following steps,
  measuring the pulse charge (Cij) delivered by a jth pulse (Pij) deposited onto an ith flash spot (Si),
  calculating an adjusted theoretical pulse charge (Ci(j+1)) to be deposited onto the ith flash spot by an (j+1)th pulse (Pi(j+1)) required to fit the charge planning by comparing a cumulated theoretical pulse charges ($\Sigma_{j-1}^{j}$ Cij) with a cumulated pulse charges ($\Sigma_{j=1}^{j}$ Cij) actually measured at the ith flash spot (Si) after j pulses, and
  preparing the pulsed particles accelerator for emitting the next pulse (Pi(j+1)) with the adjusted value of the theoretical pulse charge (Ci(j+1)).

In an embodiment, the treatment comprises:
  defining a mesh of M regular spots (Ri) covering an area of a projection parallel to the irradiation axis (X) of the target volume (Vt) (i.e., Vt=V−Vht) onto the projection plane (π),
  determining a regular charge planning for each regular spot (Ri), defining a value of each pulse charge (Cij) for depositing the target charge (Cti) with mi pulses, not necessarily at HDR; and
  defining a regular scanning sequence for depositing the target charges (Cti) onto each one of the M regular spots (Ri).

The present disclosure also concerns a treatment planning system (TPS) for implementing the treatment plan (TP) as defined above, the TPS comprising:

a mesh unit configured for defining a mesh of N flash spots (Si) covering an area of a projection parallel to an irradiation axis (X) substantially parallel to the beam (100) of the flash volume (Vht) onto a projection plane (H) normal to the irradiation axis (X);

a target charge unit configured for defining a target charge (Cti) for each flash spot (Si) required for depositing a target dose (Dti) onto the cells spanned by each flash spot (Si);

a flash planning unit configured for determining a theoretical flash charge planning for each flash spot (Si), defining a theoretical pulse charge (Cij) of a number (mi) of pulses required for depositing the target dose (Dti) at the cells spanned by each flash spot (Si), wherein the target charge (Cti) is equal to a sum of the number (mi) of theoretical pulse charges (Cij) irradiating a flash spot (i.e., $Cti=\Sigma_{j=1}^{mi} Cij$), or wherein the target dose (Dti) is equal to a sum of the number (mi) of pulse doses (Dij) deposited onto the cells spanned by the flash spot by each pulse charge (Cij) (i.e., $Di=\Sigma_{j=1}^{mi} Dij$); and a flash scanning sequence unit configured for defining a flash scanning sequence of the N flash spots, defining a sequence of flash spots (Si) on which the corresponding number (mi) of pulse doses (Dij) are to be deposited into the cells spanned by each flash spot.

The flash scanning sequence unit is configured for planning the following operations:

defining a number (k) of sets (5), each set (5) comprising a number n of flash spots (Si), wherein 1<n<N, for each set (5) of n combined flash spots, defining a flash scanning subsequence of the n combined flash spots, such that the distance (ds) between every first and second consecutive flash spots ((Si, S(i+1)) and (Sn, S1)) of the set is always lower than or equal to a maximum distance (dM) defined as a product of the scan speed (vs) and a dead time (td) (i.e., d<dM=vs× td), wherein the dead time (td) is a time between the end of a pulse and a beginning of a next pulse (i.e., td=Δtp−tp).

More particularly, with reference to the accompanying Figures, the present disclosure concerns a treatment device for treatment with a beam (100) of charged particles, preferably of protons, of a treatment volume (V) composed of, a target volume (Vt) including substantially only tumoral cells (3t) and of a flash volume (Vht) including healthy cells (3h) and tumoral cells (3t).

The treatment device comprises a pulsed particles accelerator and a processor.

Figure 3:
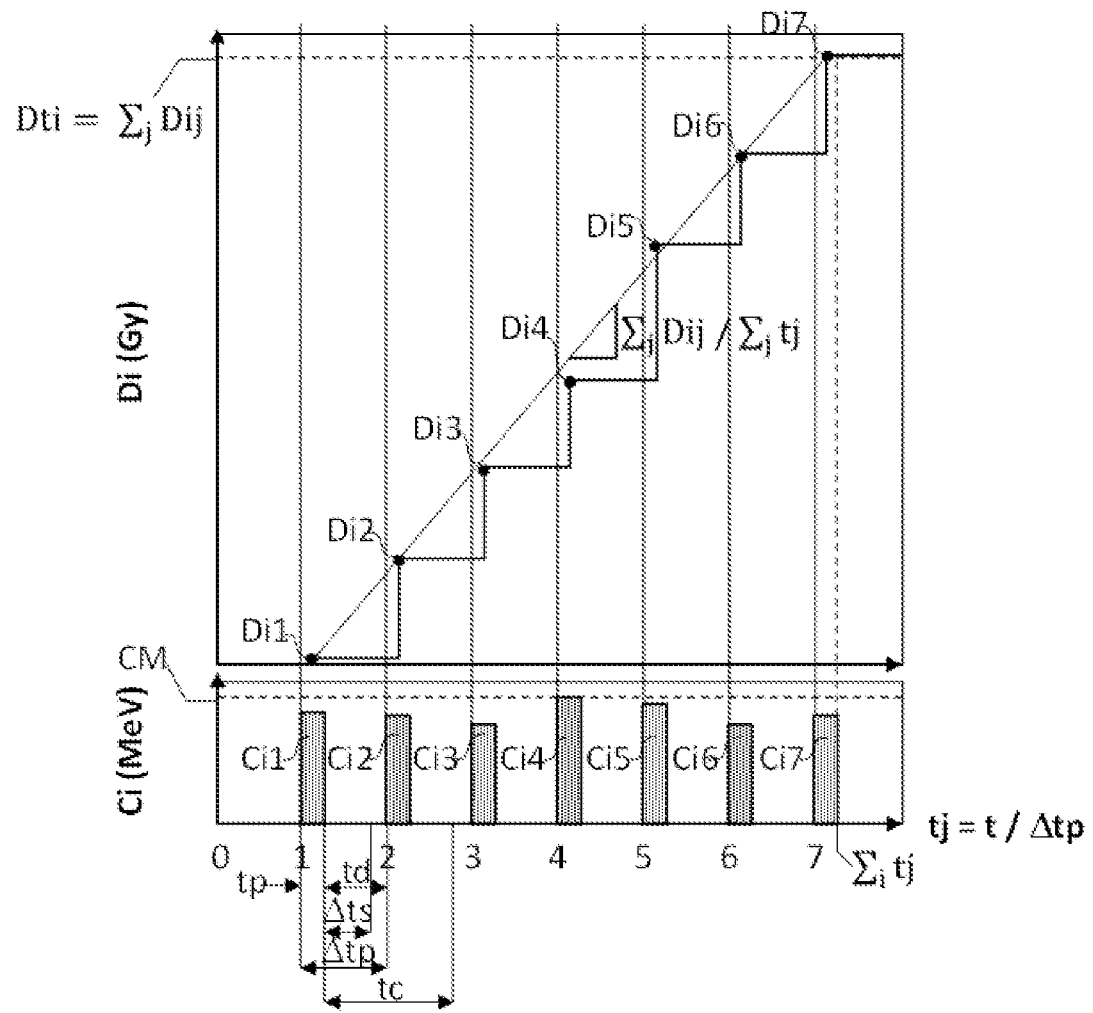
FIG. 3 shows (bottom graph) the charges of each pulse of a pulsed beam irradiating a spot (Si) with a pulsed particle accelerator by successive pulses of charges (Cij) as a function of time, and (top graph) cumulated dose ($\Sigma_j$ Dij) as a function of time.
Figure 4A:
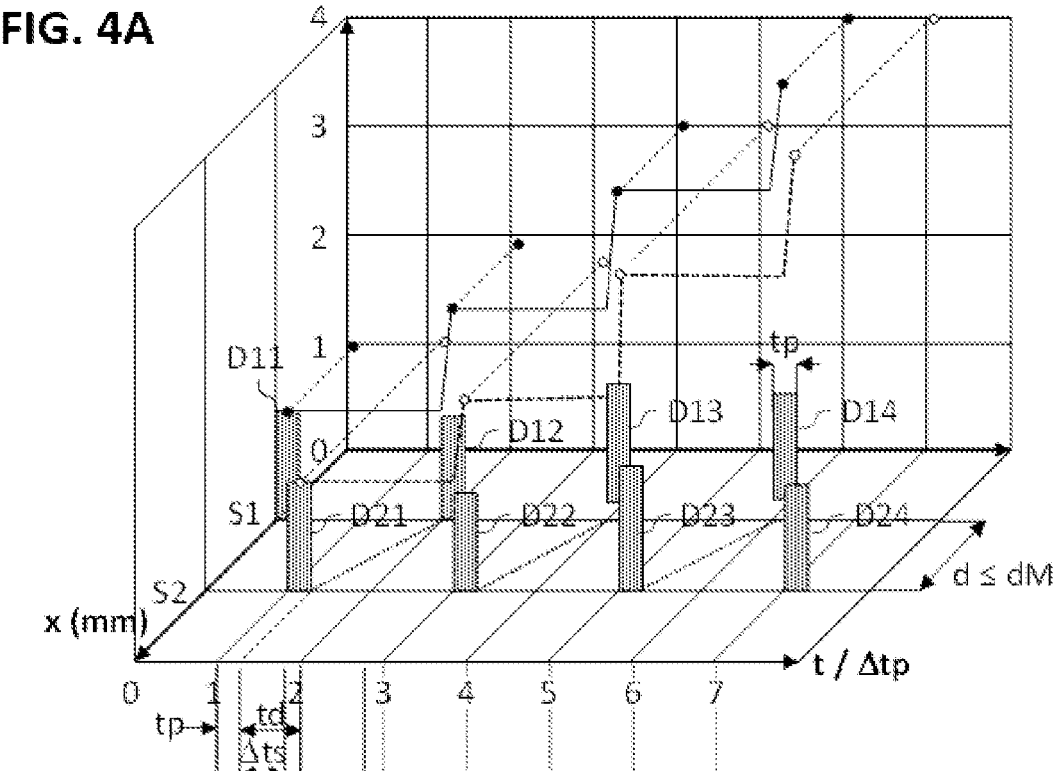
FIG. 4A illustrates a principle of the present disclosure, with successive depositions of doses into cells spanned by first and second spots (S1, S2) of a same set as a function of time.
Figure 4B:
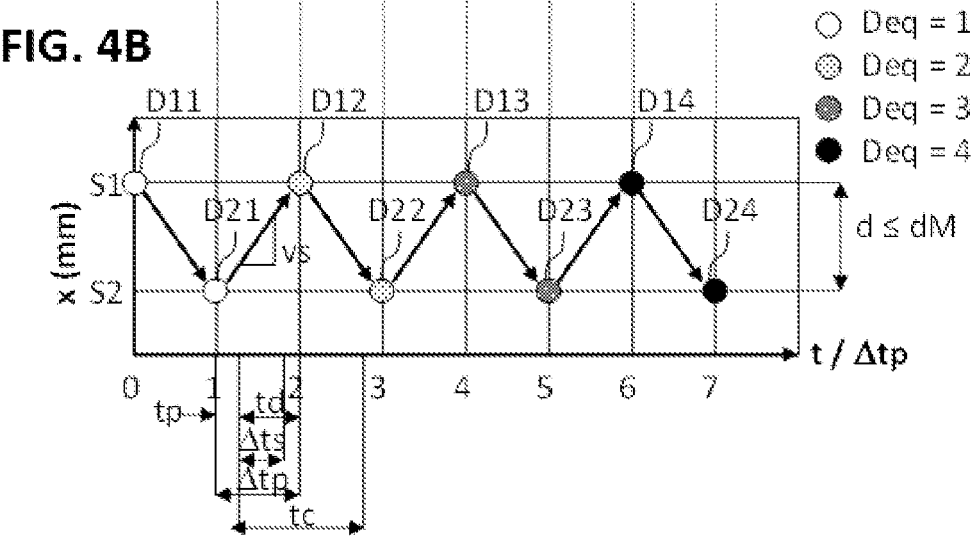
FIG. 4B shows a top view of FIG. 4A, illustrating the scanning sequence between the first and second spots (S1, S2).

The pulsed particles accelerator is configured for delivering pulses of charged particles. For example, the pulsed particles accelerator can be a synchrocyclotron, a synchrotron, or a laser driven ion accelerator. The pulsed particles accelerator is characterized by the following properties:

the charged particles are emitted by pulses (Pij), each pulse having a pulse charge (Cij) smaller than or equal to a maximum pulse charge (Cij≤CM) and a duration of pulse time (tp), and the pulses are separated from one another by an interpulse interval (Δtp) (as shown in FIGS. 3, 4A, and 5A to 5C), the beam of charged particles can scan from a first flash spot to a second flash spot at a maximum scan speed (vs=ds/Δts), wherein ds is a distance between the first and second flash spots, and Δts is a scan time required for scanning from the first to the second flash spot (as shown in FIG. 4B).

The beam can be defined by the type of charged particles to be irradiated (e.g., protons), the maximum pulse charge (CM) of a pulse (Pij), the pulse time (tp) to deliver the pulse, and the interpulse interval (Δtp) defining the time required by the particle accelerator for emitting a second pulse (Pi2) after a first pulse (Pi1) has been emitted. The number of beams and beam directions are parameters. In the present description, one beam direction only is discussed extending along an irradiation axis (X). A skilled person will appreciate that the same description can be applied mutatis mutandis to various beam directions. An SOBP can be obtained by a superposition of coaxial beamlets defining the shape of the SOBP. Alternatively, a single beam (100) can be emitted and shaped by interposing a ridge filter. These techniques are well known to the skilled person and are not explained herein.

The beams have a diameter. The charged particles are distributed over a cross section of the beam normal to the irradiation axis (X) following a Gaussian distribution. The radius of the beam can be defined as 2σ of the Gaussian distribution.

The pulsed particles accelerator is configured for depositing the doses into the treatment volume (V) by pencil beam scanning (PBS), spot by spot (Si, Ri) distributed over a single painting layer spanning the whole treatment volume (V). The doses are deposited into the cells spanned by the spots (Si) enclosed within the flash volume (Vht) at an ultra high dose deposition rate (HDR), wherein HDR is defined as a dose rate, HDR≥1 Gy/s. The doses can be deposited at any rate (CDR or HDR) in all regular spots (Ri) of the treatment volume (V) located outside of the flash volume (Vht) (as shown in FIG. 2D).

The processor is configured for controlling the pulsed particles accelerator to implement a treatment plan (TP). The TP comprises:

a definition of a mesh of N flash spots (Si);

a definition for each flash spot (Si), of a target charge (Cti) required for depositing a target dose (Dti) into the cells spanned by each flash spot (Si);

a definition of a theoretical flash charge planning for each flash spot (Si), including a theoretical pulse charge (Cij) of a number (mi) of pulses required for depositing the target dose (Dti) into the cells spanned by each flash spot (Si), wherein the target dose (Dti) is equal to a sum of the number (mi) of pulse doses (Dij) deposited into the cells spanned by the flash spot by each pulse charge (Cij) (i.e., $Di=\Sigma_{j=1}^{mi} Dij$); and a definition of a flash scanning sequence of the N flash spots, wherein the scanning sequence comprises:

a definition of a number (k) of sets (5), each set (5) comprising a number n of flash spots (Si), wherein 1<n<N, and a definition for each set (5) of n combined flash spots, of a flash scanning subsequence of the n combined flash spots, such that the distance (ds) between every first and second consecutive flash spots ((Si, S(i+1)) and (Sn, S1)) of the set is always lower than or equal to a maximum distance (dM) defined as a product of the scan speed (vs) and a dead time (td) (i.e., d≤dM=vs× td), wherein the dead time (td) is a time between the end of a pulse and a beginning of a next pulse (i.e., td=Δtp−tp).

The processor is also configured for controlling the pulsed particles accelerator such as to implement the flash scanning sequence as described in continuation.

The Mesh of Spots

Figure 2A:
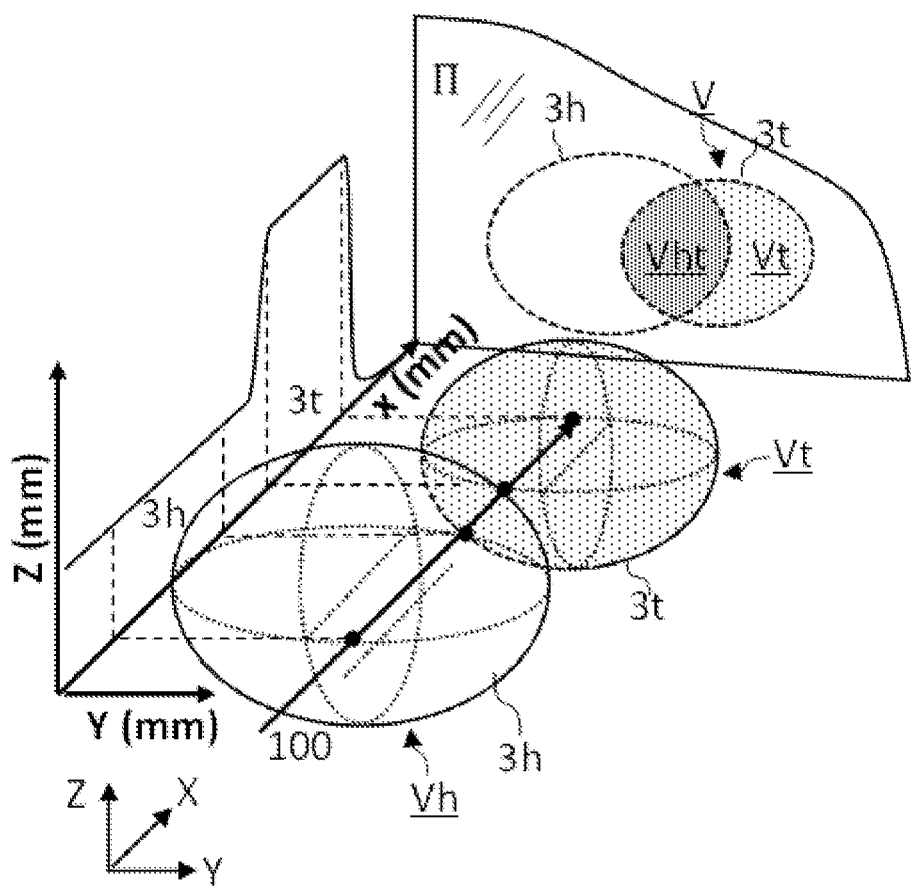
FIG. 2A shows a schematic perspective view of a system comprising a target volume with a healthy tissue located upstream thereof along the irradiation axis (X). The corresponding SOBP along the irradiation axis (X) is represented, as well as a projection of the treatment volume (V) onto a plane (H).
Figure 2B:
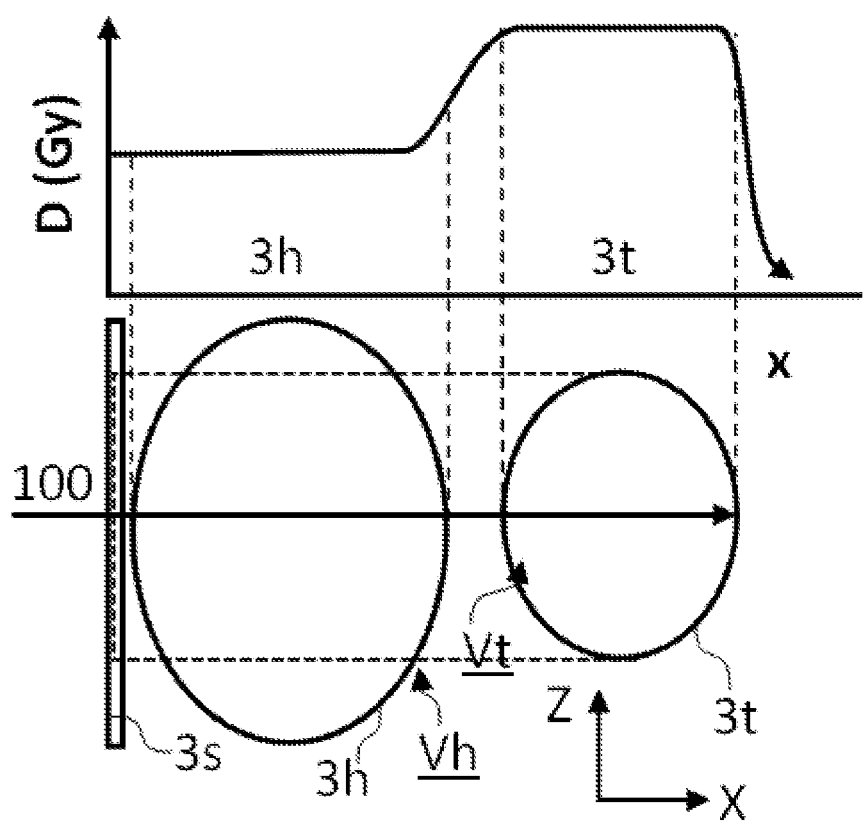
FIG. 2B shows a side view (normal to the irradiation axis (X)) of the system of FIG. 2A with corresponding SOBP.
Figures 2C, 2D:
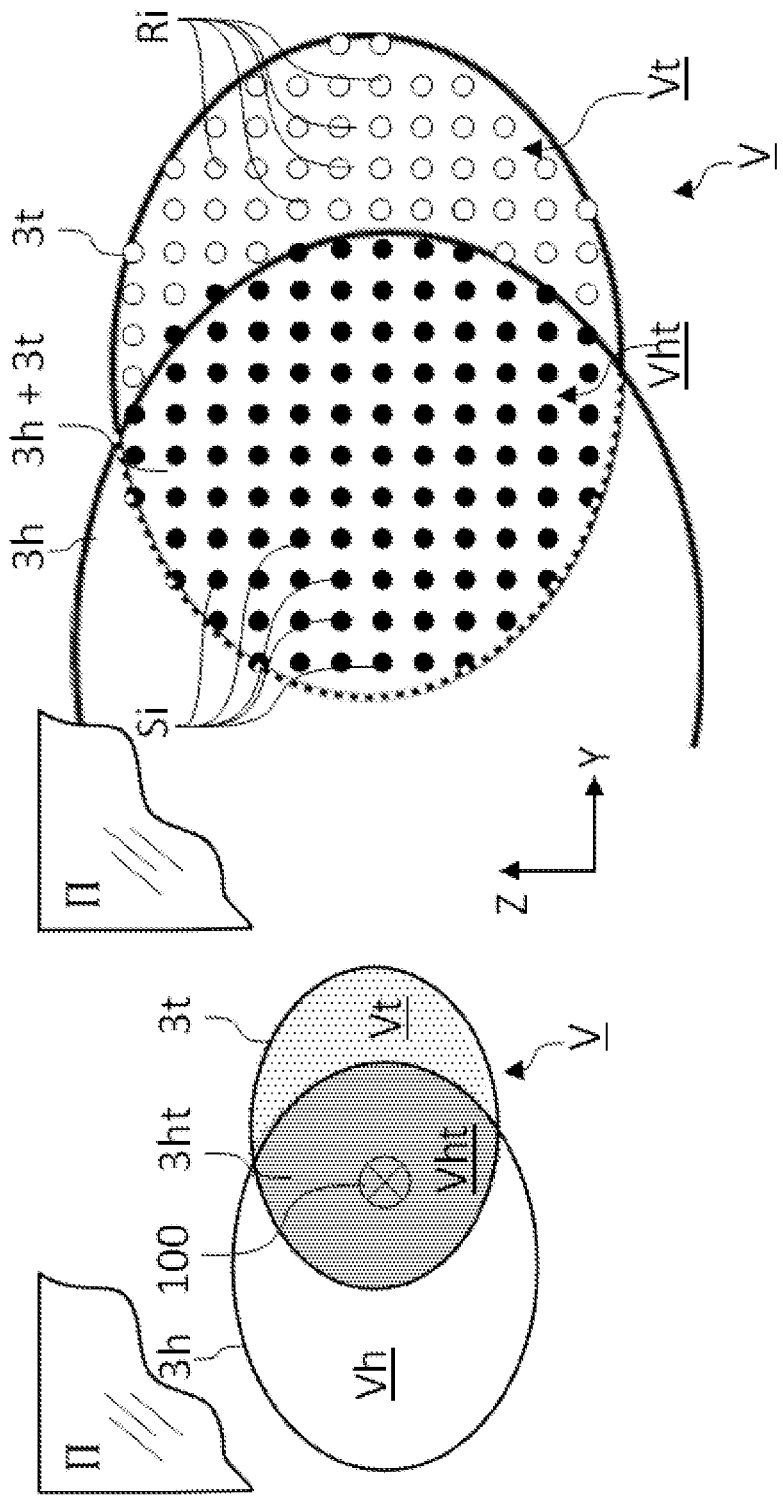
FIG. 2C shows a front view (parallel to the irradiation axis (X)) of the system of FIG. 2A.
FIG. 2D shows a detail of FIG. 2C with spots.

First, as illustrated in FIGS. 2A and 2D, a mesh of N flash spots (Si) is defined covering an area of a projection parallel to an irradiation axis (X) substantially parallel to the beam (100) of the flash volume (Vht) onto a projection plane (π) normal to the irradiation axis (X).

An oncologist characterizes the geometry and topography of the tumour region based on images of the tumour region obtained by computed tomography scan (=CT scan). FIGS. 2A-B illustrate schematically an example of a tumor region, with a healthy organ (Vh) comprising healthy cells (3h) located between a skin (3s) of a patient and a target volume (Vt) comprising mostly tumoral cells (3t). To reach the target volume (Vt), a beam (100) must cross through the healthy volume (Vh), thus irradiating both healthy cells (3h) of the healthy volume (Vh) and tumoral cells (3t) of the target volume (Vt). In some embodiments, the organ located upstream (shaded in FIG. 2A) can comprise both healthy and tumoral cells (3h, 3t), rendering impossible to target tumoral cells without irradiating healthy cells too.

In pencil beam scanning (PBS), a mesh of spots is defined, characterizing the whole volume to be irradiated. Because with the equipment available to date, in many applications it would not be possible to apply FLASH RT over the whole tumor region and in order to profit from the advantages of FLASH RT, the mesh according to the present disclosure comprises flash spots (Si), to be irradiated at HDR and regular spots (Ri) which can be irradiated at CDR. FIG. 2D shows an example of mesh comprising both flash spots (Si) (=black dots) comprised within a flash volume (Vht) and regular spots (Ri) (white dots) comprised within the target volume (Vt). In the embodiment of FIGS. 2A-2D, the flash spots (Si) are the spots aligned with beams which have to cross through the healthy organ (Vh). As mentioned above, the flash volume (Vht) may comprise healthy cells (3h) adjacent to tumoral cells (3t).

To achieve deposition at HDR over the whole flash volume (Vht), the treatment plan of the present disclosure comprises a single painting layer. For this reason, it is preferred that the flash spots (Si) enclosed in the flash volume (Vht) be aligned over the irradiation beams (X) of each beam crossing a 2D array of flash spots. The 2D array is a projection parallel to the irradiation beam (100) onto a plane normal to the irradiation beams. This way, all flash spots (Si) distributed over a depth parallel to the irradiation axis (X) of the flash volume (Vht) are comprised within a cylinder of base defined by the spots of the 2D array and of generatrixes parallel to the irradiation axis (X). The lengths of these cylinders depend on where the cylinders intersect the boundaries of the flash volume (Vht).

The spots have a dimension normal to the irradiation axis (X), which can be equal to the beam diameter discussed above. The distance between adjacent spots, defining the mesh density, is a parameter, since the denser the mesh (i.e., the closer adjacent spots are from one another) the more substantial is the effect of overlapping doses to the cells spanned by adjacent spots. A substantial overlap leading to a uniform lateral dose distribution is observed at distances between adjacent spots of about 1.5 σ.

Charge Planning

The treatment plan is directed to kill the tumoral cells present in the tumor region and spare as much as possible healthy cells adjacent to the tumoral cells or in the path of the beams aimed at the tumoral cells. The oncologist establishes a chart with the doses to be deposited in each volume. The doses deposited by a beam of given fluence depends on the type of tissue and on how it interacts with the beam. For a same tissue, it can be said that for a given tissue, the dose deposited by a beam depends mostly on the fluence of the beam (=number of charges ($C_{ij}$) per unit area). To kill the tumoral cells, a target dose ($D_{ti}$) will be deposited into the cells spanned by both flash spots (Si) and regular spots (Ri) in a session.

To spare the healthy cells, the treatment plan must satisfy the target dose rates at which doses are to be deposited locally into the flash volume (Vht) to simultaneously kill the tumoral cells and spare as much as possible the healthy cells profiting of the FLASH effect. These target dose rates are generally established by an oncologist who identifies one or more flash volumes (Vht) comprising healthy cells based on images of the tumour region obtained by computed tomography scan (=CT scan). To reach a FLASH effect in the one or more specific volumes (Vht), they must be irradiated at an ultra-high dose deposition rate (HDR), HDR at each voxel of the volume is defined as a dose deposition rate, HDR ($=\Sigma_{i,j} D_{ij}/\Sigma_j t_j \geq 1$ Gy/s) is a ratio of the sum ($\Sigma_{i,j} D_{ij}$) over all flash spots (Si) delivering dose at that voxel and all pulses ($P_{ij}$) of the doses deposited into the specified voxel of the flash volume by each pulse ($P_{ij}$), to the sum ($\Sigma_j t_j$) of the times ($t_j$) required to deposit a dose ($\Sigma_j D_{ij}$) onto one flash spot (Si) (as shown in FIG. 3). The sum of times includes the times for doses to be deposited by overlap from beams aiming at neighbouring flash spots. A voxel is a portion of tissue receiving doses from several overlapping spots. The term "voxel" is used in CT scan and can typically have dimensions of 2×2×2 mm. A voxel can therefore contain many biological cells. Since an oncologist generally relies on the results of a CT scan to define the doses to be deposited into the cells, it is reasonable to use the same term and notion also relative to the treatment plan.

To include the dose rates into the treatment plan, the performance of the particle accelerator available for carrying out the plan can be taken into account. For example, a highest dose rate ($DR_{max}$) can be defined, at which a given pulse dose ($D_{ij}$) can be delivered to a flash spot (Si) by a beam as, $DR_{max}=I_{max}\cdot K(E)$, wherein $I_{max}$ is a maximum beam current a nozzle of a proton accelerator can deliver, and $K(E)$ is a known function relating the proton fluence (number of charges (=protons) per cm2) to the dose deposited by the proton beam in the tissues for different incident energies (E) of the proton beam. For example, in Equation 26 in "Bortfeld, T. (1997) An analytical approximation of the Bragg curve for therapeutic proton beams. Med. Phys., 24 (12), 2024-2033," the factor on the right of Ø0 represents $K(E)$.

According to the present disclosure, for each flash spot (Si), a target charge ($C_{ti}$) is defined required for depositing a target dose ($D_{ti}$) onto the cells of the voxels covered by each flash spot (Si) at the end of a session. The target charge ($C_{ti}$) depends on the nature of the beam and of the tissue into which the target dose ($D_{ti}$) is to be deposited and which the beam interacts with.

Once the target charges ($C_{ti}$) for each flash spot (Si) are defined, a charge planning is determined for each flash spot (Si) to assign both number ($m_i$) and theoretical pulse charges ($C_{ij}$) of pulses to be delivered. The charge planning comprises defining a theoretical pulse charge ($C_{ij}$) of a number ($m_i$) of pulses required for depositing the target dose ($D_{ti}$) into the cells spanned by each flash spot (Si) and, ultimately, at each voxel. As illustrated in FIG. 3, the target charge ($C_{ti}$) is therefore equal to a sum of the number ($m_i$) of theoretical pulse charges ($C_{ij}$) irradiating a flash spot (i.e., $C_{ti}=\Sigma_{j=1}^{m_i} C_{ij}$). This can also be expressed in terms of doses, as the target dose ($D_{ti}$) is equal to a sum of the number ($m_i$) of pulse doses ($D_{ij}$) deposited into the cells spanned by the flash spot by each pulse charge (Cij) (i.e., $Dti=\Sigma_{j=1}^{mi} Dij$). Because of statistical uncertainties, however, the pulse charges which are actually delivered at each pulse by a particle accelerator can only be approximated to the theoretical pulse charge (Cij). It is therefore necessary to measure the value of the actual charge which has been delivered and to compare it with the value of the theoretical pulse charge (Cij). If there is a mismatch between the two values above a predefined tolerance, the theoretical pulse charge (Ci(j+1)) of the next pulse can be corrected to a new value of adjusted theoretical pulse charge, to match the (theoretical) charge planning.

A flash scanning sequence of the N flash spots is then established, defining a sequence of flash spots (Si) on which the corresponding number (mi) of pulse doses (Dij) are to be deposited into the cells spanned by each flash spot. The flash scanning sequence is established as follows.

Flash Scanning Sequence

Sets (5) of n Flash Spots

A number (k) of sets (5) of combined flash spots (Si) are defined, each set (5) comprising a number n of flash spots (Si), wherein 1<n<N. Preferably, n=2. For each set (5) of n combined flash spots, defining a flash scanning subsequence of the n combined flash spots, such that the distance (ds) between every first and second consecutive flash spots ((Si, S(i+1)) and (Sn, S1)) of the set is always lower than or equal to a maximum distance (dM) defined as a product of the scan speed (vs) and a dead time (td) (i.e., ds<dM=vs×td), wherein the dead time (td) is a time required by the particles accelerator for emitting a second pulse (Pi2) after a first pulse (Pi1) was emitted (i.e., td=Δtp−tp). Since the beam takes a time (Δts) to travel from a first to a second spot, it follows that every pair of flash spots in the scanning subsequence, must be so distanced as requiring a scanning time (Δts) not longer than the dead time (td) to scan from the first flash spot to the next flash spot in the scanning subsequence (i.e., Δts≤td, ∀ (Si, S(i+1))). The scanning subsequence proceeds as follows as illustrated in FIGS. 4A and 4B.

In an embodiment, the number (n) of combined flash spots in a set (5) is determined as follows:
- a ratio tc/td>1, if tc/td is an integer (i.e., n=tc/td, if tc/td ∈ N), and
- a sum of unity and of an integer portion of the ratio (tc/td), (i.e., n=INTEGER (tc/td)+1), in all other cases, wherein, as illustrated in FIGS. 3, 4A, 4B, 5A, and 5B, td is the dead time and tc is a computing time greater than the dead time (tc>td), required by the pulsed particles accelerator for carrying out computing operations discussed more in detail below and including defining and preparing a next pulse (P(j+1)) according to the adjusted theoretical pulse charge (Ci(j+1)) calculated on the basis of an actual pulse charge (Cij) measured on a first pulse (Pij) preceding the second pulse (Pi(j+1)), For example, if t/Δtp is comprised between 1.5 and 2.0, or between 1.6 and 1.8, the number of flash spots per set (5) can be equal to, n=2.

The number (k) of sets (5) of n combined flash spots can be an integer portion of a ratio (N/n) (i.e., n=INTEGER (N/n)), and an additional set of nR flash spots can be defined and treated as the sets of n combined flash spots as defined below, wherein nR<n is a remainder of the ratio N/n, until the target charges (Cti) has been delivered at HDR to all N flash spots of the mesh in the flash volume.

Flash Scanning Subsequence

A first pulse (P1) of pulse charge (C11) is delivered to deposit a corresponding first pulse dose (D11) into the cells spanned by a first flash spot (S1) of a first flash scanning subsequence of a first set of n combined flash spots. The actual first pulse charge (C11) actually delivered at the first flash spot (S1) is measured and compared with the theoretical first pulse charge to ensure that each spot receives the target charge (Cti) as planned. If there is a mismatch between actual and theoretical values of the first pulse charge (C11), computing an adjusted theoretical second pulse charge (C12) to be next delivered at the first flash spot (S1) to align with the theoretical flash charge planning. The measuring, comparing, and computing an adjusted value, collectively referred to as "computing operations", require a computing time (tc) to be completed. The computing time (tc) is generally larger than the interpulse interval (Δtp) separating two successive pulses of charged particles emitted by the accelerator (i.e., tc>Δtp).

After delivery of the first pulse of charge (C11) to the first spot, i.e., after the pulse time (tp), the beam is moved to a second flash spot (S2) according to the flash scanning subsequence and a first pulse charge (C21) is delivered to deposit a first pulse dose (D21) into the cells spanned by the second flash spot (S2). During that time, the computing operations for the first pulse charge (C11) to the first flash spot (S1) are being carried out during the time (tc). The beam must reach the second spot (S2) not later than when a second pulse (P2) is ready for emission, i.e., not later than the end of the interpulse interval (Δtp) between first and second pulses (P1, P2). The computing operations of measuring an actual first pulse charge (C21) delivered at the second flash spot (S2), comparing with the theoretical first pulse charge (C21), and computing an adjusted theoretical second pulse charge (C22) to be next delivered at the second flash spot (S2) are carried out, to align with the theoretical flash charge planning.

After delivery of the first pulse of charge (C21) to the second spot (S2), the beam is moved to a next flash spot (Si) in the flash scanning subsequence, and repeating the previous step (n−2) times until moving the beam to a $n^{th}$ flash spot (Sn) of the flash scanning subsequence and delivering a first pulse charge (Cn1) to deposit a first dose (Dn1) into the cells spanned by the nth flash spot. Each time the computing operations are repeated for each first dose delivered to each of the flash spots (S1–Sn) of the set (5).

During an estimated time required for measuring during a treatment session an actual first pulse charge (Cn1) delivered at the $n^{th}$ flash spot (Sn) and computing an adjusted theoretical second pulse charge (Cn2) to be next delivered at the $n^{th}$ flash spot (Sn) to align with the theoretical flash charge planning, the beam is returned to the first flash spot (S1) of the flash scanning subsequence and the adjusted theoretical second pulse dose (D12) is deposited into the cells spanned by the first flash spot (S1) thus computed at the first flash spot (S1), The same is repeated over the n flash spots to deposit the adjusted theoretical second pulse doses (Di2) to the cells spanned by each flash spot. These operations are repeated until the target charge (Cti) has been delivered to and a corresponding target dose (Dti) deposited into the cells spanned by each flash spot (S1, Sn) of the first set of n combined flash spots. If n=2, the beam moves back and forth between first and second spots (S1-S2-S1- . . . ), delivering each time a pulse, as illustrated in FIGS. 4(a) and 4(b). In FIG. 4(b) the cumulated dose Deq is normalized by adding ratios of the cumulated dose ($\Sigma_j$ Dij) to the average dose ($\overline{D_{IJ}}$) (i.e., Deq=$\Sigma_j$ Dij/$\overline{D_{IJ}}$=mi).

The beam is then moved to a first flash spot according to a second flash scanning subsequence of a second set of n combined flash spots and repeating the foregoing steps for the n combined flash spots of the second set of n combined flash spots until they all received the corresponding target dose.

Scanning Sequence of the k Sets

The n flash spots (Si) of each set (5) can be irradiated at ultra high deposition rate (HDR) as explained above. It is important to not unduly prolong the irradiation time of a flash spot (Si) already irradiated upon irradiating another spot of a different set. The sequence of the k sets must therefore also be considered to ensure that, at the end of an irradiation session, the doses (Dij) have indeed been deposited at ultra-high deposition rates (HDR). Methods for optimizing a sequence of spots to be irradiated at HDR are known in the art, such as described for example in EP20200183082. It is possible to apply any of these methods described for a sequence of spots, to a sequence of k sets. For example, a scarf sequence unit cell can be defined as described in EP20200183082.

Computing Time Larger than Interpulse Interval (tc>$\Delta$tp)

The interpulse interval ($\Delta$tp) depends exclusively on the particle accelerator used for carrying out the treatment plan. In some accelerators, several pulses can be accelerated simultaneously, separated from one another and passing through different sections of the acceleration path with different electromagnetic conditions to take account of relativistic effects. In other accelerators, a pulse must leave the accelerator before a second one can be injected and accelerated. These differences can have a substantial influence on the value of ($\Delta$tp).

The computing time (tc) on the other hand depends on the treatment installation as a whole. For example, the computing time (tc) can be required to complete at least the following steps,
  measuring the actual pulse charge (Cij) delivered by a jth pulse (Pij) deposited onto an ith flash spot (Si);
  calculating an adjusted theoretical pulse charge (Ci(j+1)) to be deposited onto the ith flash spot by an (j+1)th pulse (Pi(j+1)) required to fit the charge planning by comparing a cumulated theoretical pulse charges with a cumulated actual pulse charges ($\Sigma_{j=1}^{j}$ Cij) actually measured at the ith flash spot (Si) after j pulses; and
  preparing the pulsed particles accelerator for emitting the next pulse (Pi(j+1)) with the adjusted value of the theoretical pulse charge (Ci(j+1)).

Figure 5A:
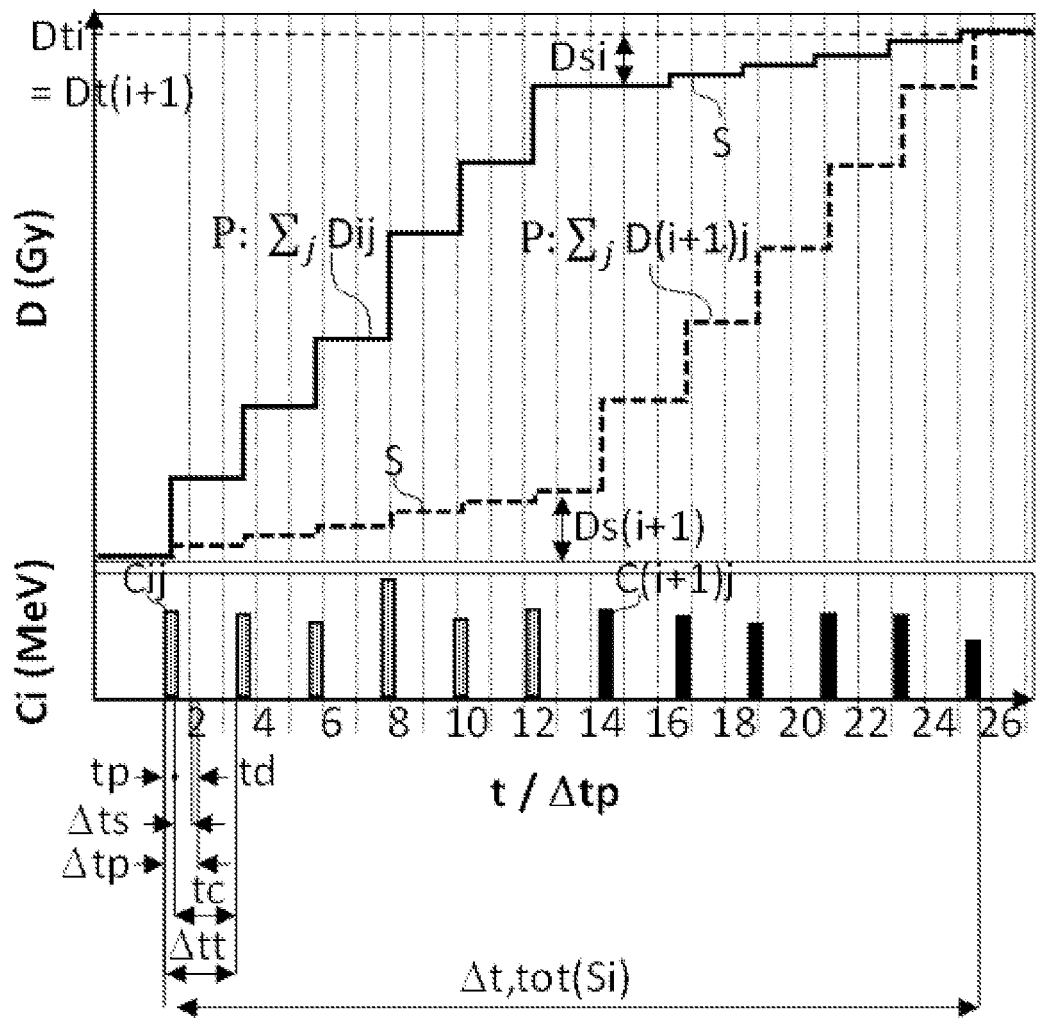
FIG. 5A shows cumulated doses deposited as a function of time into the cells spanned by first and second adjacent spots by a conventional treatment plan, irradiating the first and second spots sequentially.

Since the computing time can only start after the pulse time (tp) of duration of a pulse, for the accelerator to emit pulses at full nominal pulse rate of 1 pulse per $\Delta$tp, the computing time should be shorter than the dead time (td=$\Delta$tp−tp), required by the accelerator for emitting a second pulse. This is not possible and the computing time (tc) is greater than the free time (td) and generally larger than the interpulse interval ($\Delta$tp), i.e. (td<$\Delta$tp<tc). The computing time (tc) is therefore a dragging component of the treatment plan, as it does not allow the accelerator to function at its highest nominal pulse rate of 1 pulse/$\Delta$tp and must work instead at a lower rate of 1 pulse/$\Delta$tt, wherein $\Delta$tt=(tp+tc)>$\Delta$tp (as shown in FIG. 5A).

The present disclosure allows operating the accelerator at substantially higher rates, closer to the nominal pulse rate of 1 pulse/$\Delta$tp, for a same value of the computing time (tc).

Same Dancing Partners

Figure 6A:
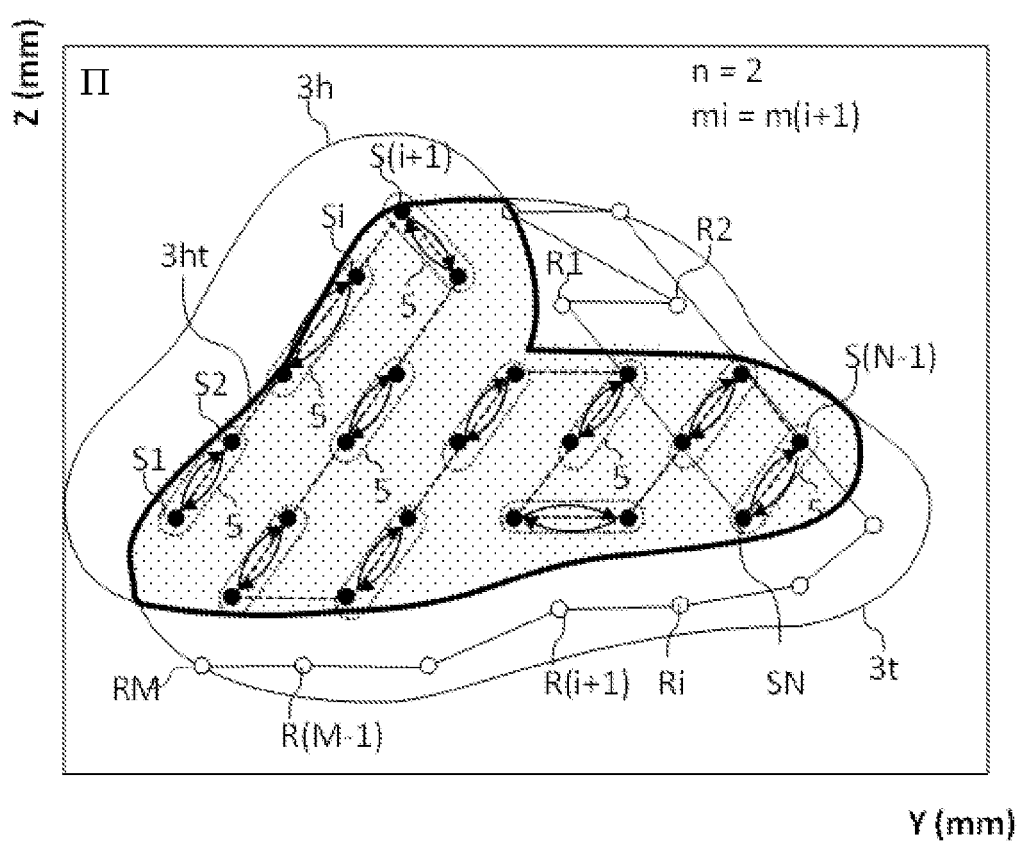
FIG. 6A shows a sequence of sets of n=2 flash spots wherein a same predefined number of pulses are to be emitted into each of the two flash spots of a set.

In one embodiment illustrated in FIG. 6A, all flash spots in a collection of sets (5) must receive a same target dose (Dti) at HDR. This would be, for example, the case in a middle portion of the flash volume (Vht), with similar characteristics and remote from any boundary or separated from one another by a distance larger than 1.5 σ with little overlap between adjacent flash spots. In any of these cases, all n flash spots of a set can receive a same number of pulses. In these conditions, the compositions of all sets of the collection of sets are constant, and the sets are composed of the same flash spots throughout the treatment session.

FIG. 6A shows an example of projected mesh on a plane (π) of flash spots (Si) (=black dots) and regular spots (Ri) (=white dots). The flash spots (Si) are combined in sets (5) of n=2 flash spots each. The cells spanned by each flash spot (Si, S(i+1)) of a same set is to receive a target dose (Dti, Dt(i+1)) deposited in a same number of pulses (i.e., mi=m(i+1)). The flash spots of two different sets (5), however, do not necessarily have to receive the same number of pulses (mi). The first set (5) is composed of first and second flash spots (S1, S2). As illustrated in FIGS. 4(a) and 4(b), with each pulse (Pij), the beam (100) commutes back and forth a number (mi) of times between the first and second flash spots of the first set (5), each time depositing a charge which cumulates until the target dose (Dti, Dt(i+1)) is reached after (mi=m(i+1)) pulses. At this stage, the cells spanned by the flash spots of the first set (5) have received the target dose (Dti) planned for the session, and the beam can travel to the second set (5) composed of third and fourth flash spots (S3, S4) and repeat the dose deposition ballet between the two spots as described above. The same operation is repeated until the last set (5) composed of the (N−1)$^{th}$ and N$^{th}$ flash spots (S(N−1), SN) to complete the treatment of the flash spots comprised within the flash volume. If the flash volume comprises an odd number (N) of flash spots, the last set (5) of n=2 flash spots is composed of the (N−2)$^{th}$ and (N−1)$^{th}$ flash spots. The N$^{th}$ flash spots is treated alone as an additional set of nR=1 flash spot and treated as the previous k (=(N−1)/2) sets of n=2 combined flash spots. The regular spots (Ri) (=white dots) can be treated at CDR as usual and as well known by the skilled person.

An advantage of the present disclosure is illustrated by comparing FIGS. 5A (prior art) and 5B (present disclosure), illustrating the cumulated dose deposited into the cells spanned by adjacent first and second flash spots (Si, S(i+1)) by (mi, m(i+1)) pulses (Pij, P(i+1)j) as a function of time. The doses accumulated onto the first spot (Si) are represented with a solid line, and the ones accumulated onto the second spot (S(i+1)) are represented with a dashed line. In the embodiment illustrated in FIGS. 5A and 5B, the first and second spots of the set (5) are close enough so that some of the doses deposited into the cells spanned by one of the first or second spot (Si, S(i+1)) overlaps with the other adjacent spot (S(i+1), Si). The doses deposited by overlap are illustrated by the portions of curves labelled (S). The doses deposited by a pulse (Pij) aimed at the first or second spot are illustrated by the portions of curves labelled (P).

FIG. 5A shows an irradiation treatment of adjacent first and second spots, as is currently performed, wherein the first and second spots are irradiated successively. The cells spanned by first spot (Si) receive (mi) pulses (Pij), depositing a cumulated dose ($\Sigma_j$ Dij). Taking account of portions of the doses to be deposited onto the cells spanned by the second spot (S(i+1)) which will overlap with the doses deposited into the cells spanned by the first spot (Si), the mi pulses (Pij) delivered onto the cells spanned by the first flash spot (Si) deposit a cumulated dose, $\Sigma_j$ Dij<Dti, smaller than the target dose (Dti), such as to reach the target dose (Dti) after receiving the doses overlapping from the second spot (S(i+1)). When all (mi) pulses have been delivered to the first flash spot (Si), the cumulated dose ($\Sigma_j$ Dti) has been deposited onto the first spot and an overlapped dose (Ds(i+1)) has been deposited onto the adjacent second flash spot (S(i+1)). The beam moves to the second spot (S(i+1)) and deposits successive doses (D(i+1)j) with (m(i+1)) successive pulses, until the target dose (Dt(i+1)) is deposited onto the second flash spot. During this operation, an overlapped dose (Dsi) is deposited by overlapping with the first spot (Si), thus reaching the target dose (Dti) too.

It can be seen that, in this example, depositing the target doses (Dti, Dt(i+1)) into the first and second adjacent spots took a total time of 25 time units (=t/$\Delta$tp) each. Each of the 25 time units corresponds to a time during which the particle accelerator used could have emitted 1 pulse. In this example, in the period of 25 time units, the accelerator emitted only 12 pulses (mi=6 pulses onto the first spot and m(i+1)=6 pulses onto the second spot), when 25 could have been emitted during that time, which yields an efficacy relative to the nominal rate of the accelerator of less than 50% (=12/25). This mismatch is due to the long computing time (tc) relative to the interpulse interval ($\Delta$tp) required for measuring the actual pulse charge (Cij) of each pulse emitted, compare it with the theoretical charge, and prepare the accelerator for emitting a next pulse (Pi(j+1)) with the adjusted theoretical pulse charge. This long time ($\Delta$t,tot(Si)) for depositing the target doses (Di, D(i+1)) by successive irradiations of the first and second spots (Si, S(i+1)) is detrimental to achieving HDR and, in some cases, could render FLASH RT impossible.

Figure 5B:
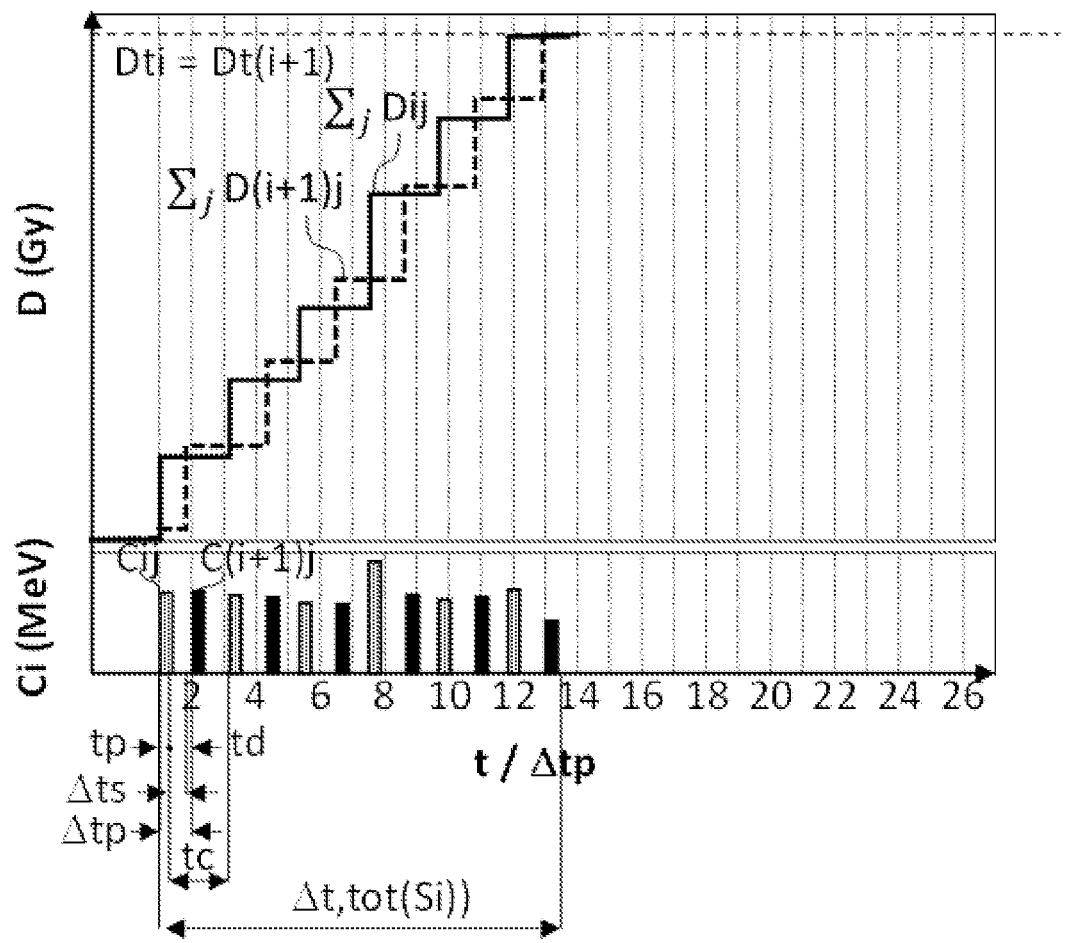
FIG. 5B shows the cumulated doses deposited as a function of time into the cells spanned by first and second adjacent spots by a first embodiment of the flash scanning sequence according to the present disclosure, with n=2.

The present disclosure allows the total irradiation time to be reduced substantially compared with the prior art treatment plan discussed above. FIG. 5B illustrates the treatment plan for a set (5) of n=2 flash spots (Si, S(i+1)), which must receive the same target doses (Dti, Dt(i+1)) and the same number of pulses (mi, m(i+1)) as in the embodiment of the prior art illustrated in FIG. 5A discussed above. As shown in FIGS. 4A and 4B, the beam deposits a first dose (D11) into the cells spanned by the first flash spot (S1), then moves to the second flash spot (S2) and deposits a first dose (D21), and back to the first flash spot (S1) to deposit a second dose (D12), according to an adjusted theoretical second pulse charge determined and prepared during the computing time (tc) as the first dose (C21) was being delivered to the second flash spot (S2). And so on. With overlap of charges from the cells spanned by one flash spot to the other, the total time ($\Delta$t,tot(Si)) required to deliver the target doses (Dti, Dt(i+1)) is about 13 unit times, i.e., about half the time required according to the prior art treatment plan discussed with reference to FIG. 5A. This yields a charge deposition rate which is twice as large as the one achieved with the prior art treatment plan, increasing the possibilities to treat a whole flash volume at HDR. Furthermore, the total time ($\Delta$t,tot (Si)), required to treat both flash spots (Si, S(i+1)) of the set (5) is also about half the time required with the prior art treatment plan. Regardless of whether there is any overlap of doses between the cells spanned by two adjacent spots, this substantially shortens the duration of a treatment session, to the benefit of the patients, and also of the hospitals and treatment centres, which can plan more treatments per unit time and thus optimize the frequency of use of the particle accelerator.

The acceleration of the treatment plan according to the present disclosure compared with the prior art treatment plan increases as a ratio (tc/td) of the computing time (tc) to the dead time (td=$\Delta$tp−tp) increases above unity. The present disclosure reduces the treatment time by selecting the number of flash spots in each set such that a ratio (tc/(td×n)) tends to unity and is preferably not lower than unity (i.e., tc/(td×n)≥1 and tc/(td×n)→1).

Different Dancing Partners

In some cases, all flash spots in a given set (5) cannot be irradiated with a same number (mi) of pulses for the cells spanned by the flash spots to reach their respective target doses (Dti). For example, this can happen for flash spots close to boundaries, or if the mesh is so dense that there is a substantial overlap between neighbouring flash spots. It follows that the cells spanned by the flash spots designed to receive the lowest number of pulses will reach their target doses (Dti) before the cells spanned by the neighbouring flash spots of a same set. These flash spots must not be irradiated anymore and must leave the dance floor, while the cells spanned by other flash spots of the same set must still receive some doses. The dose deposition can continue in that set with (n−1), (n−2), and so on flash spots, whose cells have not yet received their target doses (Dti) or their planned number of pulses (Pij), taking care of preventing any uncontrolled dose overlap towards the flash spots whose cells already received their target doses (Dti) or their planned number of pulses (Pij). As all but two flash spots left in the set have received their corresponding target doses and leave the dance floor, the flash spot among the two flash spots left, which must receive the highest number of pulses will soon be alone in the set (or on the dance floor). If the same happens with several sets, leaving too many lone dancers, it can become difficult to guarantee HDR in the whole flash volume.

Figure 6B:
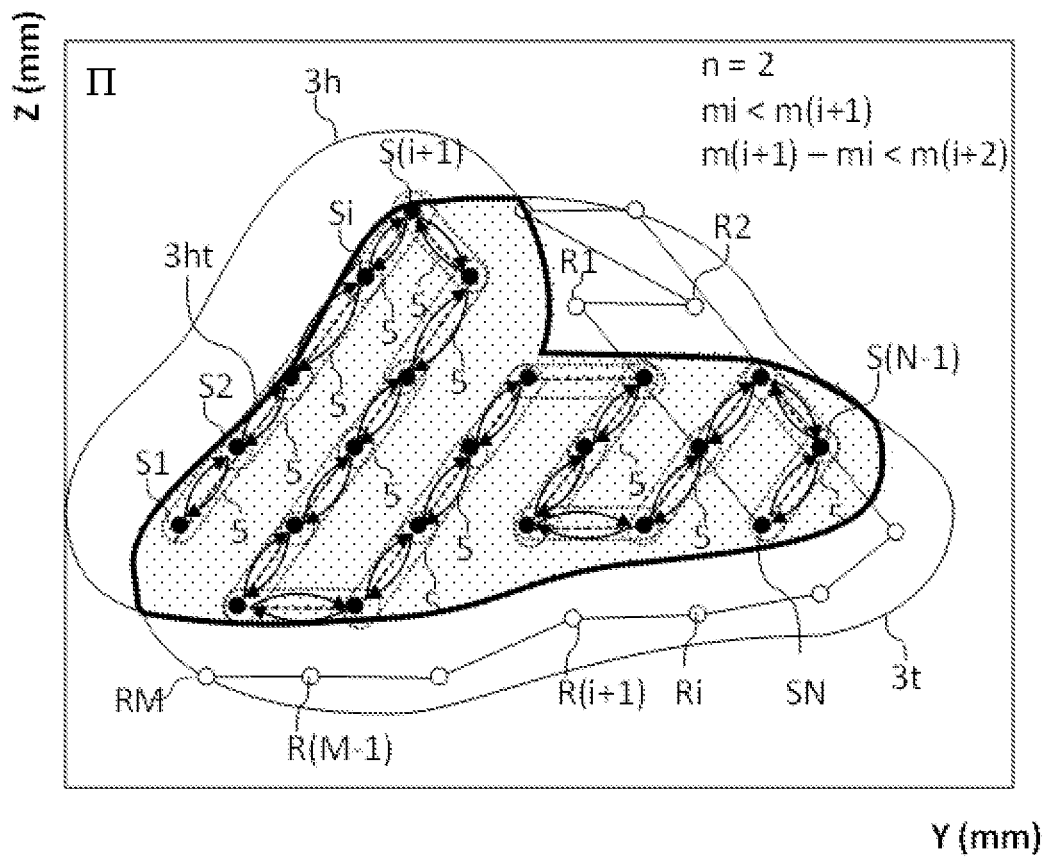
FIG. 6B shows a sequence of sets of n=2 spots wherein different target doses are to be deposited into the cells spanned by each of the two flash spots of a set.

In an embodiment of the present disclosure illustrated in FIG. 6B, a set comprises a number, n=2, of combined flash spots and the cells spanned by the second flash spot (S(i+1)) of the set must receive a higher number (m(i+1)) of pulses than the number (mi) of pulses the cells spanned by the first spot (Si) must receive to reach their respective target doses (Dti, Dt(i+1)), (i.e., mi<m(i+1)). This can be the case if the sets were attributed n=2 flash spots at the beginning of the treatment session, or because, as explained above, two flash spots only were left to receive pulse for their respective cells to reach their corresponding target doses (Dti). In this case, the different sets can be permeable, and evolve with time of treatment, by accepting new flash spots and dropping others whose cells reached their target doses (Dti). This situation can be defined as follows. A second flash spot (S2) in the flash scanning subsequence of a first set of n=2 flash spots (S1, S2) must receive a number (m2) of pulses (P21 to P2(m2)) for the cells thereof to reach a second target dose (Dt2)), which is higher than the number (m1) of pulses (P11 to P1(m1)) required to deliver a first target dose (Dt1) to the cells spanned by the first flash spot (S1) (i.e., m1<m2). This embodiment of the present disclosure proceeds as illustrated in FIG. 6B and as follows:

when the first and second flash spots (Si, S(i+1)) (as shown in solid line and dashed line of FIG. 5C) of the first set (5) have each received (mi) pulses (and in case of no substantial overlapping, the target dose (Dti) was deposited into the cells spanned by the first flash spot (Si)), the second flash spot (S(i+1)) is dissociated from the first flash spot (Si) and is combined with a third flash spot (S(i+2)) to form a second set of n=2 flash spots (S(i+1), S(i+2)), wherein the third flash spot (S(i+2)) is located at a distance d≤DM from the second flash spot (S(i+1)) and must receive a third target charge (Ct(i+2)) larger than a residual charge (Ct(i+1)−Cti), until both second flash spot (S(i+1)) and third flash spot (S(i+2)) have each received (m(i+1)−mi) pulses and the second flash spot (S(i+1)) has received the target charge (Ct(i+1)); and the third flash spot (S(i+2)) (as shown in long dashed line in FIG. 5C) is dissociated from the second flash spot (S(i+1)) and is combined with a fourth flash spot (S(i+4)) (as shown in mixed line in FIG. 5C) to form a third set of n=2 flash spots (S(i+2), S(i+3)), and so on until all N flash spots of the mesh have received their respective target charges (Cti) at HDR.

Figure 5C:
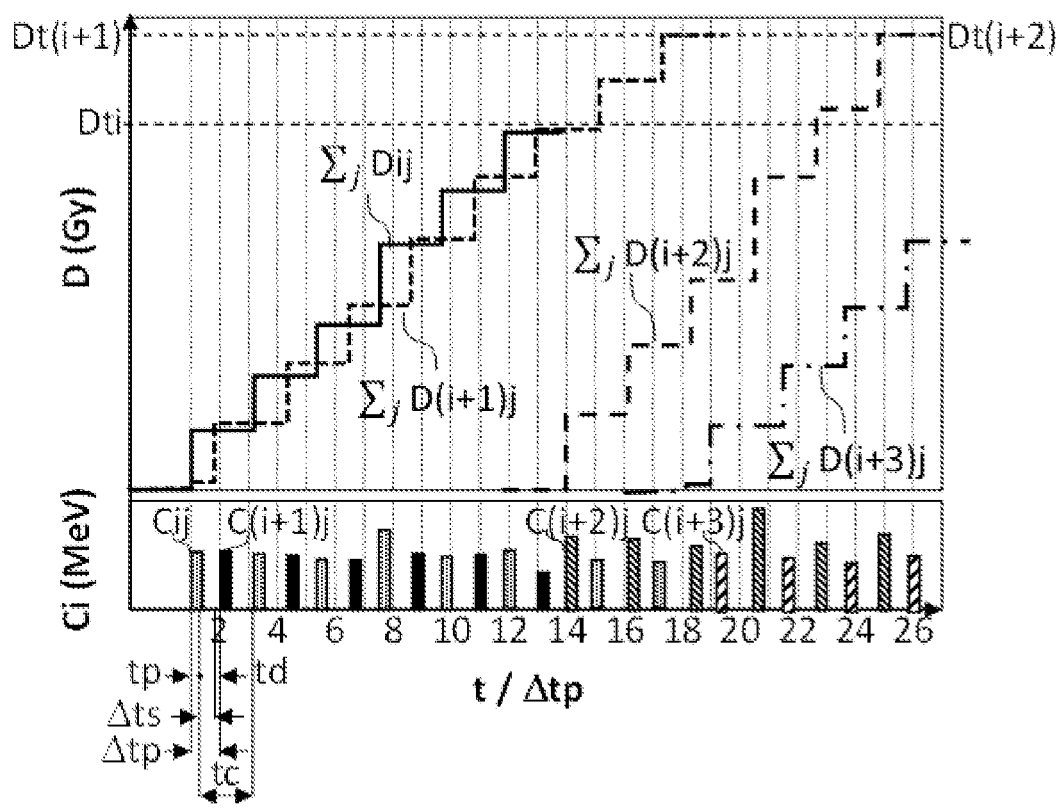
FIG. 5C shows the cumulated doses deposited as a function of time into the cells spanned by first, second, third, and fourth adjacent spots by a second embodiment of the method according to the present disclosure, with n=2.

The same analysis with respect to FIG. 5A can be done by comparing the time sequence of the prior art treatment plan with the one of the present embodiment illustrated in FIG. 5C. At the beginning the same flash scanning sequence as discussed with respect to FIG. 5B applies here, wherein the beam commutes between the first and second flash spots (Si, S(i+1)). In this embodiment, however, the cells spanned by the first flash spot (Si) reach the target dose (Dti) before the cells spanned by the second flash spot (S(i+1)). For sake of clarity, no substantial overlap between neighbouring flash spots was assumed in FIG. 5C. The second flash spot (S(i+1)) is dissociated from the first flash spot (Si) and forms a new set with a third flash spot (S(i+2)), between which the beam oscillates until the second flash spot (S(i+1)) has received its corresponding number of pulses (m(i+1)). The third flash spot (S(i+2)) dissociates from the second flash spot (S(i+1)) and is combined with a fourth flash spot (S(i+3)) to form a third set (5) of n=2 flash spots. It can be seen from FIG. 5C that the treatment time is optimized, as in the same time as required by the prior art treatment plan of FIG. 5A needed to deposit the target doses (Dti, Dt(i+1)) into the cells spanned by first and second spots (with high risk of being too slow for HDR), the target doses are deposited into the cells spanned by three flash spots (Si–S(i+2)), and partly in the cells spanned by a fourth flash spot (S(i+3)) with the present embodiment of FIG. 5C.

As discussed with regard to the embodiment of FIG. 5B above, the present disclosure reduces the treatment time by selecting the number of flash spots in each set such that a ratio (tc/(td×n)) tends to unity and is not lower than unity (i.e., tc/(td×n)≥1 and tc/(td×n)→1).

Regular Spots (Ri)

The present disclosure generally concentrates on depositing target doses (Dti) into a flash volume (Vht) at HDR. The treatment volume (V), however, also comprises a target volume (Vt) comprising predominantly tumoral cells (3t) which can be killed at CDR, because they are not adjacent to healthy cells (3h) or the beam does not traverse healthy cells to reach the target volume (Vt). The target volume (Vt) can be treated by PBS too, with no concern on the charge deposition rate, apart for shortening the session for the patients comfort. Establishing a treatment plan for the target volume (Vt) can comprise the following steps.

defining a mesh of M regular spots (Ri) covering an area of a projection parallel to the irradiation axis (X) of the target volume (Vt) (i.e., Vt=V−Vht) onto the projection plane (π);

determining a regular charge planning for each regular spot (Ri), defining a value of each pulse charge (Cij) for depositing the target charge (Cti) with mi pulses, not necessarily at HDR; and defining a regular scanning sequence for depositing the target charges (Cti) onto each one of the M regular spots (Ri).

FIGS. 6A and 6B illustrate a treatment volume (V) comprising a flash volume (Vht) defined by a mesh of flash spots (Si) represented with black dots (as discussed above), and a target volume (Vt) defined by a mesh of regular spots (Ri) represented with white dots. The treatment plan of the present disclosure treats the flash spots and the regular spots sequentially, in any order, but preferably the flash spots first followed by the regular spots, as illustrated in FIGS. 6A and 6B.

In summary, the present disclosure provides a treatment device for depositing at HDR of charged particles into a flash volume (Vht) by PBS according to a treatment plan, including a pulsed particles accelerator and a processor to control the latter. Because of the dose depositions by successive pulses and because of the statistical uncertainties on the charges (Cij) actually emitted at each pulse by the particle accelerator, a given target dose can only be deposited onto the cells spanned by a flash spot (Si) in a total time Δtt=mi×(tp+tc), at a maximum dose deposition rate of $\ominus_j$ Dij/mi×(tp+tc), which can often be too slow for yielding FLASH RT. Furthermore, for dense enough meshes, overlap of doses (Dij) deposited into the cells spanned by a first flash spot (Si) over neighbouring flash spots further prolongs the deposition time, further slowing down the dose deposition rate.

By combining the flash spots (Si) into sets of n flash spots each, and commuting the beam (100) according to a flash scanning subsequence as discussed above, the time for depositing a target dose (Dti) into the cells spanned by a flash spot (Si) is considerably shortened, and the dose deposition rate increased accordingly. This is even more advantageous when substantial dose overlap occurs between neighbouring flash spots. In all cases, the duration of a session is substantially shortened with a treatment plan as described herein, rather than with a conventional plan wherein a target dose (Dti) is deposited onto the cells spanned by each spot successively (as shown in FIGS. 5A (Prior art) and 5B and 5C (present disclosure).

| REF | DESCRIPTION |
| --- | --- |
| 3h | Healthy cell |
| 3t | Tumoral cell |
| 3s | Patient's skin |
| 5 | Set of combined flash spots |
| 100 | Beam |
| Cij | Charge of a pulse (Pij) |
| CDR | Conventional dose deposition rate |
| CM | Maximum pulse charge of a pulse |
| Di | Dose deposited in the cells spanned by a flash spot (==$\Sigma_{j=1}^{mi}$ Dij) |
| Dij | Dose deposited by a pulse Pij of charge Cij |
| d | Distance between two spots |
| dM | Max. distance between two successive flash spots of a scanning subsequence |

-continued

| REF | DESCRIPTION |
|---|---|
| ds | Scan distance |
| Dti | Target dose in the cells spanned by a spot (Si, Ri) |
| HDR | Ultra-high dose deposition rate |
| k | Number of sets |
| M | Number of regular spots (Ri) |
| mi | Number of pulses required to deposit the target dose (Dti) |
| n | Number of flash spots in a set |
| N | Number of flash spots (Si) |
| nR | Number of flash spots in an additional set (=remainder of the ratio N/n) |
| Pij | Pulse of charge (Cij) |
| Ri | Regular spot i |
| Si | Flash spot i |
| SOBP | Sum Of Bragg Peaks |
| tc | Computing time |
| td | Dead time (=$\Delta$tp − tp) |
| tp | Pulse time |
| V | Treatment volume |
| Vht | Flash volume |
| vs | Scan speed |
| Vt | Target volume |
| X | Irradiation axis |
| $\Delta$tp | Interpulse interval |
| $\Delta$ts | Scan time |

What is claimed is:

1. A treatment device for treatment with a beam (100) of charged particles of a treatment volume (V), the treatment volume (V) comprising a target volume (Vt) including substantially only tumoral cells (3*t*) and a flash volume (Vht) including healthy cells (3*h*) and tumoral cells (et), the treatment device comprising:

a pulsed particles accelerator configured to deliver pulses of charged particles for depositing doses (Dij) into the treatment volume (V) by pencil beam scanning (PBS), spot by spot (Si, Ri) distributed over a single painting layer spanning the whole treatment volume (V), such that the doses are deposited into the spots (Si) enclosed within the flash volume (Vht) at a ultra high dose deposition rate (HDR), wherein HDR is defined as a dose rate, HDR≥1 Gy/s, wherein, the charged particles are emitted by pulses (Pij), each pulse having a pulse charge (Cij) smaller than or equal to a maximum pulse charge (CM) and a duration of pulse time (tp), and the pulses are separated from one another by an interpulse interval ($\Delta$tp), and the beam of charged particles can scan from a first flash spot to a second flash spot at a maximum scan speed (vs=ds/$\Delta$ts), wherein ds is a distance between the first and second flash spots, and $\Delta$ts is a scan time required for scanning from the first to the second flash spot; and a processor configured to control the pulsed particles accelerator to implement a treatment plan (TP), wherein the treatment plan comprises:

a definition of a mesh of N flash spots (Si) covering an area of a projection parallel to an irradiation axis (X) substantially parallel to the beam (100) of the flash volume (Vht) onto a projection plane (H) normal to the irradiation axis (X);

a definition for each flash spot (Si), of a target charge (Cti) required for depositing a target dose (Dti) into the cells spanned by each flash spot (Si);

a definition of a theoretical flash charge planning for each flash spot (Si), including a theoretical pulse charge (Cij) of a number (mi) of pulses required for depositing the target dose (Dti) into the cells spanned by each flash spot (Si), wherein the target charge (Cti) is equal to a sum of the number (mi) of theoretical pulse charges (Cij) irradiating a flash spot (i.e., Cti=$\Sigma_{j=1}^{mi}$Cij), or wherein the target dose (Dti) is equal to a sum of the number (mi) of pulse doses (Dij) deposited into the cells spanned by the flash spot by each pulse charge (Cij) (i.e., Di=$\Sigma_{j=1}^{mi}$ Dij); and a definition of a flash scanning sequence of the N flash spots, including a sequence of flash spots (Si) on which the corresponding number (mi) of pulse doses (Dij) are to be deposited into the cells spanned by each flash spot, wherein the flash scanning sequence comprises:

a definition of a number (k) of sets, each set comprising a number n of flash spots (Si), wherein 1<n<N; and a definition for each set of n combined flash spots, of a flash scanning subsequence of the n combined flash spots, such that the distance (ds) between every first and second consecutive flash spots ((Si, S(i+1)) and (Sn, S1)) of the set is always lower than or equal to a maximum distance (dM) defined as a product of the scan speed (vs) and a dead time (td) (i.e., d≤dM=vs×td), wherein the dead time (td) is a time between the end of a pulse and a beginning of a next pulse (i.e., td=$\Delta$tp−tp), and wherein the processor is configured for controlling the pulsed particles accelerator to:

(a) point the beam at a first flash spot (S1), i.e, i=1, and deliver a first pulse charge (C11), i.e., with j=1, to deposit a corresponding first pulse dose (D11) into the cells spanned by a first flash spot (S1) of a first flash scanning subsequence of a first set of n combined flash spots;

(b) move the beam to a second flash spot (S2) of the flash scanning subsequence, i.e, i=2, and deliver a first pulse charge (C21) to deposit a first pulse dose (D21) into the cells spanned by the second flash spot (S2) during an estimated time required for measuring during a treatment session an actual first pulse charge (C11) actually delivered at the first flash spot (S1) and compute an adjusted theoretical second pulse charge (C12) to be next delivered at the first flash spot (Si) to align with the theoretical flash charge planning;

(c) if i<n, move the beam to an ith flash spot (Si) in the flash scanning subsequence, deliver a first pulse charge (Ci1) into the cells spanned by the ith flash spot (Si) during an estimated time required for measuring during a treatment session an actual previous pulse charge (C(i−1)1) actually delivered at a previous flash spot (S(i−1)) and compute an adjusted theoretical second pulse charge (C(i−1)2) to be next delivered at the previous flash spot (S(i−1)) to align with the theoretical flash charge planning;

(d) repeat the previous step (n−3) times until i=n;

(e) return the beam to the first flash spot (S1) of the flash scanning subsequence, and deposit the adjusted theoretical second pulse charge (C12) thus computed at the first flash spot (S1), during an estimated time required for measuring during a treatment session an actual first pulse charge (Cn1) delivered at the nth flash spot (Sn) and computing an adjusted theoretical second pulse charge (Cn2) to be next delivered at the nth flash spot (Sn) to align with the theoretical flash charge planning;

(f) repeat (b) to (e) until j=(mi−1) and repeat (b) to (d) for j=mi, at least until the target charge (Cti) has been delivered to each flash spot (S1, Sn) of the first set of n combined flash spots;

(g) move the beam to a first flash spot according to a second flash scanning subsequence of a second set of n combined flash spots and repeat (a) to (f) for the n combined flash spots of the second set of n combined flash spots; and (h) repeat a last step to the flash scanning subsequences of the remaining (k−2) sets of n combined flash spots until the corresponding target charges (Cti) is delivered at HDR to the n combined flash spots of all k sets of the mesh.

2. The treatment device of claim 1, wherein, the number (n) of combined flash spots in a set is, a ratio tc/td>1, if tc/td is an integer (i.e., n=tc/td, if tc/td ∈ N); and a sum of unity and of an integer portion of the ratio (tc/td), (i.e., n=INTEGER(tc/td)+1), in all other cases, wherein td is the dead time and tc is a computing time greater than the dead time (tc>td), required by the pulsed particles accelerator for defining and preparing a next pulse (P(j+1)) according to the adjusted theoretical pulse charge (Ci(j+1)) calculated on the basis of an actual pulse charge (Cij) measured on a first pulse (Pij) preceding the second pulse (Pi(j+1)).

3. The treatment device of claim 2, wherein the processor is configured to complete at least the following within the computing time (tc):

measure the pulse charge (Cij) delivered by a jth pulse (Pij) deposited onto an ith flash spot (Si);

calculate an adjusted theoretical pulse charge (Ci(j+1)) to be deposited onto the ith flash spot by an (j+1)th pulse (Pi(j+1)) required to fit the charge planning by comparing a cumulated theoretical pulse charges ($\Sigma_{j=1}^{j} C_{ij}$) with a cumulated pulse charges ($\Sigma_{j=1}^{j} C_{ij}$) actually measured at the ith flash spot (Si) after j pulses; and prepare the pulsed particles accelerator for emitting the next pulse (Pi(j+1)) with the adjusted value of the theoretical pulse charge (Ci(j+1)).

4. The treatment device according to claim 1, 2, or 3, wherein the number (k) of sets of n combined flash spots is an integer portion of a ratio (N/n) (i.e., n=INTEGER (N/n)), and an additional set of nR flash spots is defined and treated as the sets of n combined flash spots, wherein nR<n is a remainder of the ratio N/n, until the target charges (Cti) has been delivered at HDR to all N flash spots of the mesh.

5. The treatment device according to claim 1, 2, or 3, wherein the flash scanning sequence comprises:

the number (n) of combined flash spots for all of the k sets is 2 (i.e., n=2);

the second flash spot (S2) in the flash scanning subsequence of a first set of n=2 flash spots (S1, S2) receives a number (m2) of pulses (P1 to Pm2) to reach a second target charge (Ct2)), which is higher than the number (m1) of pulses (P1 to Pm1) required to deliver a first target charge (Ct1) to the first flash spot (S1) (i.e., m1<m2 and Ct1<Ct2);

wherein the processor is configured for controlling the pulsed particles accelerator to:

dissociate the second flash spot (S2) from the first flash spot (S1) when the first and second flash spots (Si, S2) of the first set (5) have each received m1 pulses and the target charge (Ct1) was delivered to the first flash spot (S1);

combine the second flash spot (S2) with a third flash spot (S3) to form a second set of n=2 flash spots (S2, S3), wherein the third flash spot (S3) is located at a distance d≤DM from the second flash spot (S2) and receives a third target charge (Ct3) larger than a residual charge (Ct2−Ct1), until both second flash spot (S2) and third flash spot (S3) have each received (m2−m1) pulses and the second flash spot (S2) has received the target charge (Ct2); and dissociate the third flash spot (S3) from the second flash spot (S2) and combine the third flash spot (S3) with a fourth flash spot (S4) to form a third set of n=2 flash spots (S3, S4), and so on until all N flash spots of the mesh have received their target charges (Cti) at HDR.

6. The treatment device according to claim 1, 2, or 3, wherein the treatment plan comprises:

a definition of a mesh of M regular spots (Ri) covering an area of a projection parallel to the irradiation axis (X) of the target volume (Vt) (i.e., Vt=V−Vht) onto the projection plane (π);

a regular charge planning for each regular spot (Ri), defining a value of each pulse charge (Cij) for depositing the target charge (Cti) with mi pulses, not necessarily at HDR; and a definition of a regular scanning sequence for depositing the target charges (Cti) onto each one of the M regular spots (Ri).

7. A treatment planning system (TPS) for implementing the treatment plan (TP) as defined in claim 1, 2, or 3, the TPS comprising:

a mesh unit configured to define a mesh of N flash spots (Si) covering an area of a projection parallel to an irradiation axis (X) substantially parallel to the beam (100) of the flash volume (Vht) onto a projection plane (π) normal to the irradiation axis (X);

a target charge unit configured to define a target charge (Cti) for each flash spot (Si) required for depositing a target dose (Dti) into the cells spanned by each flash spot (Si);

a flash planning unit configured to determine a theoretical flash charge planning for each flash spot (Si), and define a theoretical pulse charge (Cij) of a number (mi) of pulses required for depositing the target dose (Dti) into the cells spanned by each flash spot (Si), wherein the target charge (Cti) is equal to a sum of the number (mi) of theoretical pulse charges (Cij) irradiating a flash spot (i.e., $C_{ti}=\Sigma_{j=1}^{mi} C_{ij}$), or wherein the target dose (Dti) is equal to a sum of the number (mi) of pulse doses (Dij) deposited into the cells spanned by the flash spot by each pulse charge (Cij) (i.e., $D_i=\Sigma_{j=1}^{mi} D_{ij}$); and a flash scanning sequence unit configured to define a flash scanning sequence of the N flash spots, defining a sequence of flash spots (Si) on which the corresponding number (mi) of pulse doses (Dij) are to be deposited into the cells spanned by each flash spot, wherein the flash scanning sequence unit is configured to plan the following operations:

defining a number (k) of sets, each set comprising a number n of flash spots (Si), wherein 1<n<N;

for each set of n combined flash spots, defining a flash scanning subsequence of the n combined flash spots, such that the distance (ds) between every first and second consecutive flash spots ((Si, S(i+1)) and (Sn, S1)) of the set is always lower than or equal to a maximum distance (dM) defined as a product of the scan speed (vs) and a dead time (td) (i.e., d≤dM=vs×td), wherein the dead time (td) is a time between the end of a pulse and a beginning of a next pulse (i.e., td=Δtp−tp).

* * * * *